US012773506B2

(12) United States Patent
Davidson et al.

(10) Patent No.: US 12,773,506 B2
(45) Date of Patent: Oct. 27, 2026

(54) DEVICES AND METHODS FOR LOW LATENCY ORAL AUTHENTICATION

(71) Applicant: Echo ID Ltd, Tel Aviv-Jaffa (IL)

(72) Inventors: Perry Davidson, Tel-Aviv (IL); Oren Harel, Ashdod (IL); Yakov Yury Rovniagin, Nes-Ziona (IL); Harel Gur, Kibbutz Mefalsim (IL); Or Averbuch, Petach-Tikva (IL); Shay Landa, Tel-Aviv (IL)

(73) Assignee: Echo ID Ltd, Tel Aviv-Jaffa (IL)

( * ) Notice: Subject to any disclaimer, the term of this patent is extended or adjusted under 35 U.S.C. 154(b) by 189 days.

(21) Appl. No.: 18/379,723

(22) Filed: Oct. 13, 2023

(65) Prior Publication Data

US 2024/0033452 A1 Feb. 1, 2024

Related U.S. Application Data

(63) Continuation of application No. 17/921,670, filed as application No. PCT/IL2021/051125 on Sep. 14, 2021, now Pat. No. 11,793,956.

(30) Foreign Application Priority Data

Sep. 16, 2020 (IL) .......................................... 277423

(51) Int. Cl.
*A61M 15/06* (2006.01)
*A24F 40/51* (2020.01)
(Continued)

(52) U.S. Cl.
CPC ............. *A61M 15/06* (2013.01); *A24F 40/51* (2020.01); *A24F 40/53* (2020.01); *A24F 40/60* (2020.01);
(Continued)

(58) Field of Classification Search
None
See application file for complete search history.

(56) References Cited

U.S. PATENT DOCUMENTS 4,738,333 A 4/1988 Collier et al.
4,996,161 A 2/1991 Conners
(Continued)

FOREIGN PATENT DOCUMENTS

CA 2636115 7/2007
CN 101099411 1/2008
(Continued)

OTHER PUBLICATIONS

Notice of Reason(s) for Rejection Dated Jul. 1, 2025 From the Japan Patent Office Re. Application No. 2023-517713 and Its Translation Into English. (16 Pages).
(Continued)

*Primary Examiner* — Peter J Macchiarolo
*Assistant Examiner* — Jermaine L Jenkins

(57) ABSTRACT

A cavity authentication system for verifying a feature of a user using at least one acoustic signal, including an orifice element, including at least a signal opening and a reflection opening, an acoustic wave generator (AWG), an acoustic wave sensor (AWS), at least one output waveguide, at least one input waveguide, a processor and a memory, the AWG for producing at least one acoustic signal, the AWS for receiving at least one reflection of the acoustic signal, the output waveguide for transmitting the acoustic signal to the user, the input waveguide for receiving the reflection of the acoustic signal, wherein the processor is configured to analyze the reflection and to compare the analyzed reflection with the retrievable cavity authentication data and to gen-
(Continued)

erate an indication whether the analyzed reflection matches the retrievable cavity authentication data above a pre determined threshold.

17 Claims, 14 Drawing Sheets

(51) Int. Cl.

| | |
|---|---|
| ***A24F 40/53*** | (2020.01) |
| ***A24F 40/60*** | (2020.01) |
| ***A61K 31/00*** | (2006.01) |
| ***A61M 11/04*** | (2006.01) |
| ***A61M 15/08*** | (2006.01) |
| ***G06F 21/32*** | (2013.01) |

(52) U.S. Cl.

CPC ......... *A61K 31/658* (2023.05); *A61M 11/041* (2013.01); *A61M 15/08* (2013.01); *G06F 21/32* (2013.01); *A61M 2205/276* (2013.01); *A61M 2205/3375* (2013.01); *A61M 2205/52* (2013.01); *A61M 2205/6009* (2013.01); *A61M 2205/609* (2013.01)

(56) References Cited

U.S. PATENT DOCUMENTS

| | | | |
|---|---|---|---|
| 5,787,187 | A | 7/1998 | Bouchard et al. |
| 6,190,323 | B1 | 2/2001 | Dias et al. |
| 6,697,299 | B2 | 2/2004 | Kato et al. |
| 8,187,202 | B2 | 5/2012 | Akkermans et al. |
| 8,424,527 | B1 | 4/2013 | Kayyali et al. |
| 9,743,691 | B2 | 8/2017 | Minskoff et al. |
| 10,334,912 | B2 * | 7/2019 | Byrd ..................... A44B 15/005 |
| 11,344,686 | B2 * | 5/2022 | Pell ........................ A61L 2/0088 |
| 11,676,438 | B2 * | 6/2023 | Hubbard ................. A24F 40/53 131/328 |
| 12,424,023 | B2 * | 9/2025 | Davidson ............. G06V 40/172 |
| 2004/0215968 | A1 | 10/2004 | Rodwell |
| 2006/0130828 | A1 | 6/2006 | Sexton |
| 2008/0281169 | A1 | 11/2008 | Akkermans et al. |
| 2013/0063579 | A1 | 3/2013 | Hanina et al. |
| 2016/0106935 | A1 | 4/2016 | Sezan et al. |
| 2017/0273597 | A1 * | 9/2017 | Schuelke ................ H02J 50/80 |
| 2017/0318861 | A1 | 11/2017 | Thorens |
| 2018/0064402 | A1 | 3/2018 | Leydon |
| 2018/0085540 | A1 | 3/2018 | Dantsker et al. |
| 2018/0110939 | A1 | 4/2018 | Lanzkowsky |
| 2018/0161530 | A1 | 6/2018 | Ganton et al. |
| 2019/0150520 | A1 | 5/2019 | Fraser et al. |
| 2019/0311722 | A1 | 10/2019 | Caldwell |
| 2019/0387797 | A1 | 12/2019 | Christensen et al. |
| 2020/0000143 | A1 | 1/2020 | Anderson et al. |
| 2020/0065568 | A1 | 2/2020 | Nienhouse |
| 2020/0230998 | A1 * | 7/2020 | Edekar ................. B43K 29/004 |
| 2021/0034724 | A1 | 2/2021 | Fong et al. |
| 2021/0195981 | A1 * | 7/2021 | Ghaffarzadegan ........................... B60W 50/0098 |
| 2023/0120935 | A1 | 4/2023 | Davidson et al. |

FOREIGN PATENT DOCUMENTS

| | | | |
|---|---|---|---|
| CN | 102316919 | 1/2012 | |
| CN | 103546622 | 1/2014 | |
| CN | 104688321 | 6/2015 | |
| CN | 109982589 | 7/2019 | |
| CN | 110975088 | 4/2020 | |
| EP | 0625023 | 4/1999 | |
| EP | 3342442 | 7/2018 | |
| EP | 3468648 | 5/2020 | |
| JP | 2009-509575 | 3/2009 | |
| JP | 2015-180255 | 10/2015 | |
| KR | 10-2007-0106964 | 11/2007 | |
| RU | 2720566 | 5/2020 | |
| WO | WO 2017/175218 | 10/2017 | |
| WO | WO 2017/216516 | 12/2017 | |
| WO | WO 2018/160073 | 9/2018 | |
| WO | WO 2018/213746 | 11/2018 | |
| WO | WO 2020/183470 | 9/2020 | |
| WO | WO 2020/183476 | 9/2020 | |
| WO | WO 2020/183478 | 9/2020 | |
| WO | WO-2020183476 A1 * | 9/2020 | ............. G16H 40/60 |
| WO | WO 2022/059007 | 3/2022 | |

OTHER PUBLICATIONS

English Translation of Office Action Dated Feb. 11, 2022 From the Israel Patent Office Re. Application No. 277423. (8 Pages).

International Preliminary Report on Patentability Mar. 30, 2023 From the International Bureau of WIPO Re. Application No. PCT IL2021/051125. (9 Pages).

International Search Report and the Written Opinion Dated Nov. 28, 2021 From the International Searching Authority Re. Application No. PCT/IL2021/051125. (17 Pages).

Notice of Allowance Dated Jun. 20, 2023 from the US Patent and Trademark Office Re. U.S. Appl. No. 17/921,670. (7 pages).

Office Action Dated Sep. 30, 2021 From the Israel Patent Office Re. Application No. 277423. (7 Pages).

Official Action Dated May 10, 2023 From the US Patent and Trademark Office Re. U.S. Appl. No. 17/921,670. (25 Pages).

Notification of Office Action and Search Report Dated Jul. 17, 2025 From the State Intellectual Property Office of the People's Republic of China Re. Application No. 202180076092.X with its Summary and Machine Translation of the Office Action into English. (18 Pages).

Supplementary European Search Report and the European Search Opinion Dated Aug. 12, 2024 From the European Patent Office Re. Application No. 21868881.0. (7 Pages).

Request for Examination and Search Report Dated Jan. 20, 2025 From the (ROSPATENT), The Federal Service for Intellectual Property, Patents and Trademarks of the Russian Federation Re. Application No. 2023109512 and its Machine Translation of Examination Report into English. (42 Pages).

Notice of Reason(s) for Rejection Dated Mar. 3, 2026 From the Japan Patent Office Re. Application No. 2023-517713 and Its Translation Into English. (6 Pages).

Notification of Office Action and Search Report Dated Apr. 30, 2026 From the State Intellectual Property Office of the People's Republic of China Re. Application No. 202180076092.X with its Summary and Machine Translation of the Office Action into English. (18 Pages).

Communication Pursuant to Article 94(3) EPC Dated Aug. 4, 2026 From the European Patent Office Re. Application No. 21868881.0 (9 Pages).

Examination Report Dated Jun. 23, 2026 From the Australian Government, IP Australia Re. Application No. 2021342819. (4 Pages).

* cited by examiner

DEVICES AND METHODS FOR LOW LATENCY ORAL AUTHENTICATION

RELATED APPLICATIONS

This application is a continuation of U.S. patent application Ser. No. 17/921,670 filed on Oct. 27, 2022, which is a National Phase of PCT Patent Application No. PCT/IL2021/051125 having International Filing Date of Sep. 14, 2021, which claims the benefit of priority of Israel Patent Application No. 277423 filed on Sep. 16, 2020. The contents of the above applications are all incorporated by reference as if fully set forth herein in their entirety.

FIELD OF THE DISCLOSED TECHNIQUE

The disclosed technique relates to oral authentication devices and methods, in general, and to methods, devices and systems which operate and function based on an oral authentication, in particular.

BACKGROUND OF THE DISCLOSED TECHNIQUE

Many electronic devices exist in the market which operate by entry of the device into a cavity of a human user, such as an oral cavity, a nasal cavity or a tympanic cavity. Such devices can include devices into which a user either exhales (i.e., blows air from their lungs) such as medical exhalation devices (e.g., CPAP machines, BIPAP machines, respirators with an exhalation valve and the like) and breathalyzers, inhales (i.e., breathes in either air or a substance in gas or aerosol form) such as an inhaler, an electronic cigarette, a vaporizer and the like, or simply places the device in the cavity such as an oral thermometer or a tympanic thermometer. Collectively, such devices can be referred to as electronic devices for use in a human cavity.

Whereas unauthorized use of some of these electronic devices for use in a human cavity bears no real or significant potential for abuse (such as in the case of unauthorized use of a thermometer), some of these electronic devices can be easily abused once purchased (for example, an underage individual using an electronic cigarette belonging to an adult and use of an inhaler by an individual to inhale prescription drugs prescribed for another individual). There is thus a need to provide additional levels of security and authorization to prevent abuse of such devices, such as access to controlled substances by minors or unauthorized users.

Whereas identification and verification systems are known in the art for electronic devices in general, such as by use of a login name and password or even by using distinctive biometric identifiers of an individual (such as fingerprint scanning, face recognition, iris/retina recognition and even voice patterns), each of these identification and verification systems is vulnerable to being bypassed with or without the knowledge of the original user. For example, login names and passwords can be hacked and distinctive biometric identifiers can be duplicated, such as by photography (for visual features) and recordings (for voice patterns). There is thus a need for identification and verification systems for electronic devices for use in a human cavity which cannot be easily duplicated and bypassed.

Known in the art are devices which are designated to use an oral authentication to identify and verify an individual as an authorized user of an aerosol generating system, such as an electronic cigarette. European patent application no. EP 3 342 442 A1 to JT International S. A., entitled "AEROSOL GENERATING SYSTEM AND METHOD OF CONTROLLING THE OPERATION OF AN AEROSOL GENERATING SYSTEM" is directed towards a system comprising a vaporizer and an electronic circuit for activating and deactivating the vaporizer. The system also includes a signal emitter and a signal receiver as well as an authorization controller. The signal emitter emits an electroacoustic signal into an oral cavity of a user and the signal receiver receives reflected electroacoustic response signals from the oral cavity. A profile of the received reflected response signals is compared to a pre-determined response signal profile stored in the system. According to this publication, the results of the comparison can be used by the authentication controller to activate or deactivate the vaporizer, thus controlling the authorized use of the system with a distinctive biometric identifier that is difficult to reproduce.

The system of EP 3 342 442 A1 does not provide an identification and verification system for use with an electronic device for use in a human cavity which can identify and verify an authorized user as compared to an unauthorized user without prior registration. An authorized user may be categorized as a general group of users (such as adults over the age of 18), however, to use the above system, prior registration is required. It is also desirable that the identification and verification process be of sufficiently low latency so as not to impact the user experience of an electronic device for use in a human cavity.

SUMMARY OF THE PRESENT DISCLOSED TECHNIQUE

It is an object of the disclosed technique to provide a novel method and system for identification and verification using acoustic signals, useful for electronic devices for use in a human cavity or human orifice. In accordance with the disclosed technique, there is thus provided a cavity authentication system for verifying at least one feature of a user using at least one acoustic signal. The cavity authentication system includes an orifice element, an acoustic wave generator, an acoustic wave sensor, at least one output acoustic waveguide, at least one input acoustic waveguide, a processor, a memory and a power supply. The orifice element includes at least an acoustic signal opening and a reflection signal opening. The output acoustic waveguide is coupled between the acoustic wave generator and the acoustic signal opening and the input acoustic waveguide is coupled between the acoustic wave sensor and the reflection signal opening. The processor is coupled with the acoustic wave generator and the acoustic wave sensor and the power supply is coupled with the acoustic wave generator, the acoustic wave sensor and the processor. The acoustic wave generator is for producing the acoustic signal and the acoustic wave sensor is for receiving at least one reflection of the acoustic signal. The output acoustic waveguide is for transmitting the acoustic signal to the user and the input acoustic waveguide is for receiving the reflection of the acoustic signal. The processor is for processing the reflection of the acoustic signal and the memory is configured to store cavity authentication data representative of the feature which is retrievable by the processor. The processor is configured to analyze the reflection and to compare the analyzed reflection with the retrievable cavity authentication data stored in the memory and to generate an indication whether the analyzed reflection matches the retrievable cavity authentication data above a pre-determined threshold.

In accordance with an aspect of the disclosed technique, there is thus provided an inhalation system for delivering a substance to a user. The inhalation system includes an inhalation device and a replaceable component, attachable and detachable from the inhalation device. The inhalation device includes an acoustic wave generator, an acoustic wave sensor, an acoustic seal, a processor, a memory and a power supply. The processor is coupled with the acoustic wave generator and the acoustic wave sensor and the power supply is coupled with the acoustic wave generator, the acoustic wave sensor and the processor. The acoustic wave generator is for producing at least one acoustic signal and the acoustic wave sensor is for receiving at least one reflection of the acoustic signal. The processor is for processing the reflection of the acoustic signal and the memory is configured to store cavity authentication data representative of the user which is retrievable by the processor. The replaceable component includes an inhalation element, a container, at least one hollow, at least one output acoustic waveguide and at least one input acoustic waveguide. The inhalation element includes at least an inhalation opening, an acoustic signal opening and a reflection signal opening. The container is coupled with the inhalation element and the hollow is positioned between the container and the inhalation opening. The output acoustic waveguide is configured to connect between the acoustic wave generator and the acoustic signal opening and the input acoustic waveguide is configured to connect between the acoustic wave sensor and the reflection signal opening. The acoustic seal is coupled with the output acoustic waveguide and the input acoustic waveguide when the replaceable component is attached to the inhalation device. The container is for storing the substance, the hollow is for delivering the substance, the output acoustic waveguide is for transmitting the acoustic signal to the user and the input acoustic waveguide is configured to receive the reflection of the acoustic signal. The acoustic seal is for acoustically sealing the acoustic wave generator and the acoustic waves sensor respectively with the output acoustic waveguide and the input acoustic waveguide. The processor is configured to analyze the reflection and to compare the analyzed reflection with retrievable cavity authentication data stored in the memory and to generate an indication whether the analyzed reflection matches the retrievable cavity authentication data above a pre-determined threshold.

In accordance with an aspect of the disclosed technique, there is thus provided a replaceable component containing a substance, configured to be attachable and detachable from an inhalation device. The replaceable component includes an inhalation element, a container, at least one hollow, at least one output acoustic waveguide and at least one input acoustic waveguide. The inhalation element includes at least an inhalation opening, an acoustic signal opening and a reflection signal opening. The container is coupled with the inhalation element and the hollow is positioned between the container and the inhalation opening. The output acoustic waveguide is configured to connect between an acoustic wave generator in the inhalation device and the acoustic signal opening and the input acoustic waveguide is configured to connect between an acoustic wave sensor in the inhalation device and the reflection signal opening. The container is for storing the substance and the hollow is for delivering the substance to a user.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
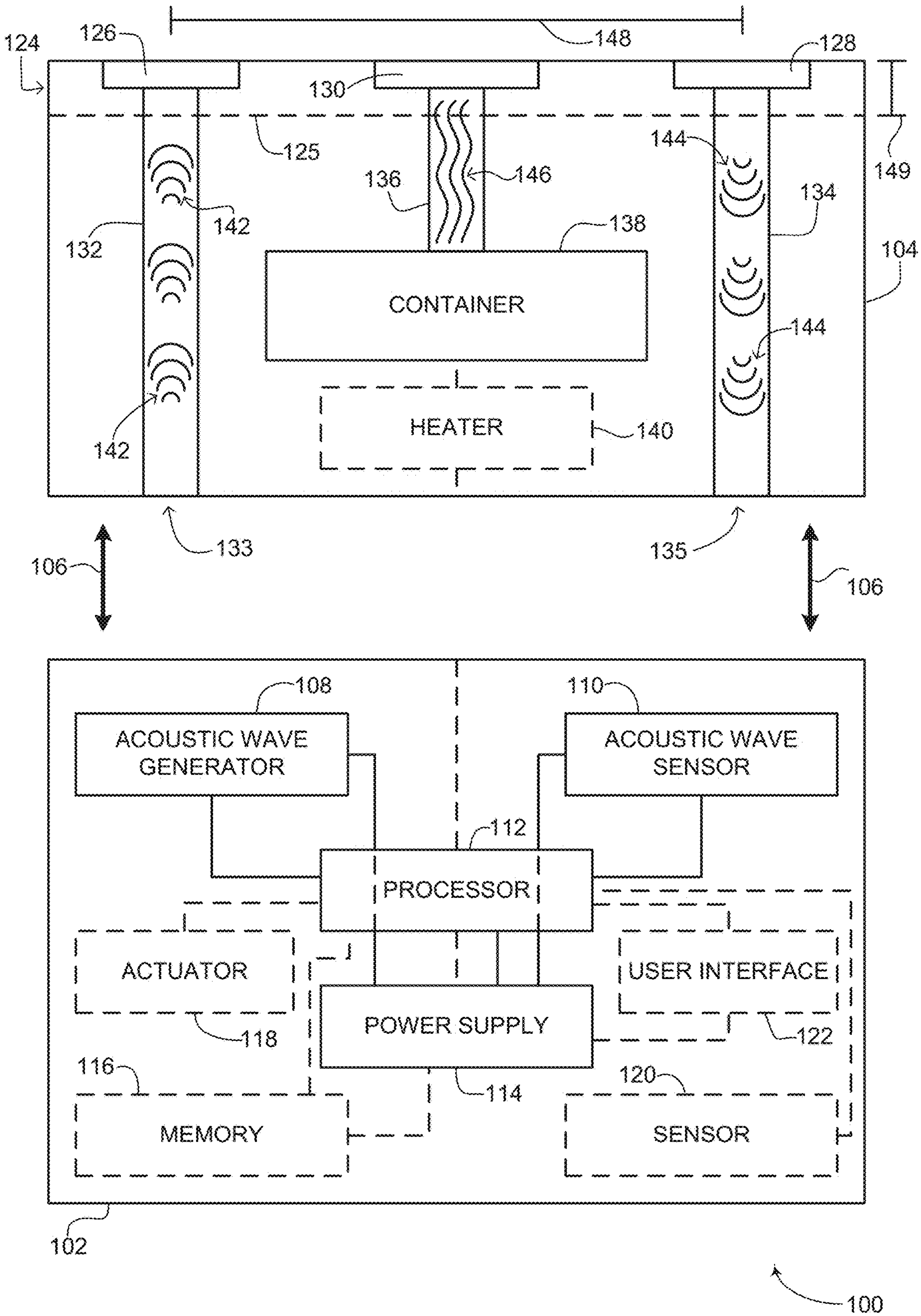
FIG. 1 is a schematic illustration of an inhalation system, constructed and operative in accordance with an embodiment of the disclosed technique.

The disclosed technique provides novel identification and verification methods and systems, which are useful for electronic devices for use in a human cavity or human orifice. An embodiment of the disclosed technique enables such electronic devices to execute either one of or both of identification verification (herein abbreviated ID) and age verification (herein abbreviated AV) of a user with low latency so as not to impact, or to minimally impact, the user experience of such electronic devices. According to an embodiment of the disclosed technique, acoustic waves in a frequency range of 1.5 kilohertz up to 9 kilohertz (herein abbreviated KHz) are used to establish a unique signature of a human cavity for a given individual (such as in the case of ID) and/or to establish unique features forming a signature of a human cavity for a group of individuals based on age (such as in the case of AV). The signature can then be used by such electronic devices to authenticate a user and thus enable or disable a function of the electronic device. According to an embodiment of the disclosed technique, acoustic waves in a frequency range below 1.5 KHz may specifically be used. In addition, according to an embodiment of the disclosed technique acoustic waves in a frequency range above 9 KHz may specifically be used.

The disclosed technique can be used with any electronic device for use in a human cavity or orifice, whether that cavity be the oral cavity (i.e., the mouth), the nasal cavity (i.e., the nose) or the tympanic cavity (i.e., the ear) and can include exhalation devices (i.e., devices that function by exhaling), inhalation devices (i.e., devices that function by inhaling) as well as devices which don't require either inhalation or exhalation (for example, devices which are placed in the tympanic cavity and devices which are simply placed in the mouth or nose). For example, the disclosed technique can be used with electronic devices such as electronic wind musical instruments, medical exhalation devices, such as continuous positive airway pressure ("CPAP") and bilevel positive airway pressure ("BIPAP" or BPAP") machines and respirators with an exhalation valve, and breathalyzers (examples of exhalation devices), an electronic cigarette (herein abbreviated e-cigarette), a vaporizer, a vaping device, a dry herb vaporizer and an inhaler (examples of inhalation devices) as well oral and tympanic thermometers (examples of devices which don't require inhalation or exhalation).

In an embodiment, the electronic device functions to authenticate the individual through the human cavity and to control the operation of an associated device. The associated device can be in communication with the electronic device performing the authentication, by wired and/or wireless communication. Thus the disclosed technique can be used for the purpose of authenticating a user based on a signature of the user's cavity. In this embodiment, the device of the disclosed technique can be used for merely authenticating a user, with the authentication being linked to control access and/or to operate a separate device which is in communication (either wired and/or wirelessly) with the device of the disclosed technique. As a first example, the device of the disclosed technique may be embodied as a probe which can communicate with an electronic lock, wherein successful authentication of the user by the device provides a signal to open the electronic lock (for example, in the case of a door). Such an embodiment could be used to gain access to restricted areas in a complex or building and could even be used as a means for border control. As a second example, the device of the disclosed technique may be embodied as a dongle for a computer or may be embodied as a device in communication with a dongle for a computer. Successful authentication of the user by the device can then provide a signal to either grant access to the computer, grant access to data, grant access to a website, grant access to a server, permit the performance of an action via the computer (e.g., transfer funds in a bank account) and the like. In such an embodiment, the device may communicate with the dongle via a wired connection or a wireless communication protocol, such as Bluetooth™. In the embodiment of the disclosed technique used for general authentication purposes, the disclosed technique can be used for authenticating a user for using any electronic device having communication abilities. Thus the disclosed technique can be embodied as a dongle-like device which can provide ID and/or AV as described herein via a wired and/or wireless communication to a controlled electronic device.

A signature of the human cavity (herein referred to as a cavity signature) is established by transmitting at least one acoustic signal in one of the aforementioned frequency ranges of the disclosed technique into the human cavity and receiving at least one reflection of the acoustic signal from the human cavity. Subsequent transmissions of the acoustic signal into the human cavity and received reflections of the acoustic signal (herein referred to as a cavity sample) can then be used to authenticate a user by comparing the cavity sample of the received reflections to a stored cavity signature of the user, thus performing ID. In the case of the cavity signature being of the oral cavity, the signature can be referred to as an oral signature. The term "oral signature" is substantially used throughout the description to describe an embodiment of the disclosed technique wherein an oral signature is used as part of the disclosed technique. However, such description should not be construed as limiting and is merely brought as an example embodiment of the disclosed technique, which can be used for the purposes of authenticating and validating any human cavity as mentioned above via a cavity signature. According to the disclosed technique, a plurality of cavity signatures of users in a specified age group can be used to establish unique features for a cavity signature for a specified age group. Thus subsequent transmissions of the acoustic signal and received reflections of the acoustic signal (i.e., cavity samples) can then be used to authenticate a permitted user by comparing the features of the cavity sample received to stored features of the cavity signature of a permitted user. In addition, age related specific features can be calculated and determined for a user signature age group and a cavity sample as compared to the cavity signature can then be used to estimate the user's age group, thus performing AV. According to the disclosed technique this is achieved by sampling the cavity signatures of a plurality of users and using the samples with machine learning tools and algorithms to establish unique features for a specified age group. The specified age groups might be binary, such as permitted users (adults over a given age, such as 18) and non-permitted users (individuals being under a given age, such as minors under the age of 18), as well as more varied groups, such as child users (minors under the age of 14), adolescent users (minors between the ages of 14-16, 14-18, 16-18 and the like), adult users over the age of 18 and adult users over the age of 21.

According to the disclosed technique, the ability to establish a cavity signature and use it for authentication in the case of ID and even more so in the case of AV is related to the frequency range of the acoustic signal transmitted to the human cavity as well as the general quality and signal-to-noise ratio (herein abbreviated SNR) of the transmitted acoustic signal and the received reflection of the acoustic signal. The inventors have discovered that the quality of the reflections of acoustic signals received from the human cavity vary depending on frequency and that certain frequency ranges generate higher quality reflections of acoustic signals with higher SNR and thus from which more accurate features can be discerned in order to establish a cavity signature according to the disclosed technique. The inventors have also discovered that different frequency ranges may be preferable over others depending on the use of the disclosed technique as explained below. Frequencies in the ultrasound range, for example those above 20 KHz, substantially produce very low quality reflected signals unless the element of the electronic device which transmits the ultrasound signal is physically touching a wall of the human cavity. And even in such a case, such ultrasound signals are energetically inefficient as compared to acoustic signals. The inventors have thus discovered that the use of ultrasound to generate an oral signature will only function with substantial effectiveness if such devices are placed within and/or flush against the oral cavity such that they are touching the surface of the mouth. According to the disclosed technique, acoustic signals within the audible range of 20 hertz (herein abbreviated Hz) to 20 KHz are transmitted to the human cavity to establish a cavity signature and then to generate cavity samples to perform ID and/or AV without the requirement of having the electronic device physically touch any surface of the human cavity, whether internal or external. Thus in an embodiment, the transmission of acoustic signals is performed without any direct contact between an opening of a waveguide of the device with any portion of the human cavity (e.g., the device is placed within the mouth and possibly held in place by the lips and/or teeth, but avoids direct contact with the tongue and/or teeth). The inventors have further discovered that even within the frequency range of audible sound, in an embodiment, the frequency range between 1.5 KHz up to 9 KHz provides acoustic signal reflections which provide the most amount of unique features between users when establishing a cavity signature. This is particularly important when establishing an oral signature (i.e., a cavity signature of the mouth), as higher frequencies above 9 KHz are significantly more sensitive to the position within the oral cavity from which a cavity sample is taken and to any movement in and/or change of shape of the oral cavity (e.g., through breathing, movement of the tongue, movement of the jaw muscles and the like) while a cavity sample is taken. Thus even though the disclosed technique can use any audible sound acoustic signal to establish a cavity signature, a range of 1.5 KHz up to 9 KHz or a range of 1.5 KHz up to 5 KHz may preferably be used as the transmitted acoustic signal. The range of 1.5-9 KHz for the acoustic signal may provide optimal performance and results in inhalation system 100. A shorter range of 1.5-5 KHz for the acoustic signal may be used if implementation constraints require it, such as waveguides that do not support higher frequencies, hardware limitations and the like. The inventors have also discovered that using an acoustic signal with frequencies above 9 KHz (and up to 20 KHz) can provide very precise information for discerning features in a human cavity that does not significantly change shape, such as the nasal cavity and the tympanic cavity. Thus in an embodiment of the disclosed technique, wherein a nasal signature and/or a tympanic signature is used to establish a cavity signature, the acoustic signals used for the cavity signature and the cavity sample may be within the frequency range of 9 KHz up to 20 KHz. The inventors have further discovered that acoustic signals below 1.5 KHz may be less effective from an energy standpoint for establishing a cavity signature, for example because high transmission power of the acoustic signal in that frequency range is required to establish a high enough SNR over ambient noise, such as a user's breathing. The transmission power required in such a case would make the transmitted acoustic signal audible to a user and possibly even a bystander, thereby lowering the user experience of a device of the disclosed technique (for example, if the disclosed technique is embodied as an e-cigarette), and a larger sound generator (such as a speaker) would be needed in such a case. However in an embodiment where the audibility of the transmitted acoustic signal and/or the size of the sound generator are not design constraints (for example, in the case of a medical exhalation device), the acoustic signal may have a frequency range of 20 Hz to 9 KHz, and optionally even acoustic signals in the frequency range of 20 Hz to 1.5 KHz may be used to improve the discernability of features of the user's cavity signature. In an embodiment, it may be preferred to transmit a sound that is audible, at least to the user. Optionally, this is performed to suit the user's personal preference or enjoyment. In an embodiment, the audible sound may be used to alert a user that a given total amount of substance was or is about to be delivered. This may ensure adherence to a desired regimen and/or reduce the likelihood of an unintentional overdose or excessive use. Optionally, a notification is delivered in such circumstances to a user interface. The sound heard by the user may overlap and/or be distinct in frequency, composition and/or time in comparison to the signal used to obtain the cavity signature. In an embodiment, this sound is adjusted to the user's hearing capability and/or preference.

Another aspect of the quality of the transmitted acoustic signal and the acoustic signal reflections from the human cavity relates to the path travelled by the acoustic signal from the sound generator which creates the sound, to the sensor which detects the reflections of the sound. According to the disclosed technique, waveguides are used to couple the sound generator to a first opening in the electronic device which is placed in the human cavity to transmit the acoustic signal and to couple the sensor which receives and detects the reflections of the sound to a second opening in the electronic device which is also placed in the human cavity. The use of waveguides also increases the design and placement possibilities of the sound generator and sensor within the electronic device. In addition, the inventors have discovered that the use of waveguides which are acoustically sealed to both the sound generator and sensor as well as the first and second openings described above significantly increases the SNR and thus the quality of the transmitted acoustic signal as well as of the reflections of the acoustic signal such that unique features of the cavity signature of a user can be discerned, both in the case of ID and AV.

A further aspect of the disclosed technique relates to the volume of the transmitted acoustic signal. As the electronic device of the disclosed technique is placed inside a human cavity for use, such as in the mouth, nose or ear, the main source of noise which can potentially interfere with the transmitted acoustic signal is noise emanating from inside the body relating to the respiratory system. This can be the ambient noise coming from the lungs as air is inhaled and/or exhaled as well as noises created by the throat (such as when a person coughs or clears their throat) or nose (such as when a person sneezes or sniffs). According to an embodiment of the disclosed technique, in order for a cavity signature to be established, the intensity level of the transmitted acoustic signal is substantially higher than any recurring noise source in the human cavity, which in general is the ambient noise generated as a person breathes. Thus even though there may be a desire to transmit a very low intensity acoustic signal to authenticate a user, which will be almost undetected by the user (such as the intensity level of a user's breath while in a resting position and not during strenuous physical activity), the intensity level of the transmitted signal should be high enough so as to allow for a high enough SNR to generate a cavity signature with discernable features. Also, according to an embodiment of the disclosed technique, the intensity level of the transmitted acoustic signal is lower than a threshold at which an SNR is provided which is too low to generate a cavity signature with discernable features. The inventors have discovered that if the intensity level of the transmitted acoustic signal is too high, the intensity level of the reflected acoustic signals causes receiver compression (colloquially known as a ringing effect) in the sensor receiving the reflected acoustic signal, thereby causing a significant decrease in SNR and significantly lowering the discernability of the features in the cavity signature. Thus according to the disclosed technique, the intensity level of the transmitted acoustic signal should be sufficiently high to achieve a high enough SNR above the ambient noise of a user's breathing while being below an intensity threshold at which receiver compression occurs (i.e., below or softer than a receiver compression threshold) in the sensor receiving and detecting the reflected acoustic signals. For example, in an embodiment of the disclosed technique designed as an e-cigarette, the intensity level of the transmitted acoustic signal could be between 46-100 dB SPL (sound pressure level in decibels) or equivalently between 0.004-2 newtons per square meter (herein abbreviated N/m 2).

Reference is now made to FIG. 1, which is a schematic illustration of an inhalation system, generally referenced 100, constructed and operative in accordance with an embodiment of the disclosed technique. Inhalation system 100 includes an inhalation device 102 and a replaceable component 104. As shown schematically, replaceable component 104 can be coupled and attached, as well as decoupled and detached from inhalation device 102, as shown by plurality of arrows 106. Details of the coupling and decoupling of replaceable component 104 with inhalation device 102 are described below. Inhalation device 102 includes an acoustic wave generator 108, an acoustic wave sensor 110, a processor 112 and a power supply 114. Inhalation device 102 can also include a memory 116, an actuator 118, a sensor 120 and a user interface 122, each of which are optional components and are illustrated with dotted lines. Processor 112 is coupled with acoustic wave generator 108, acoustic wave sensor 110 and power supply 114 and can optionally be coupled with memory 116, actuator 118, sensor 120 and user interface 122. Power supply 114 is coupled with acoustic wave generator 108 and acoustic wave sensor 110 and can optionally be coupled with memory 116 and user interface 122.

Replaceable component 104 includes an acoustic signal opening 126, a reflection signal opening 128, an inhalation opening 130, an output acoustic waveguide 132, an input acoustic waveguide 134, a delivery tube 136 and a container 138. Acoustic signal opening 126, reflection signal opening 128 and inhalation opening 130 can together be considered an inhalation element 124, demarcated by a dotted line 125. Inhalation element 124 can also be referred to as a mouthpiece or an orifice element and represents the portion of replaceable component 104 which is inserted into the user's oral cavity when inhalation system 100 is to be used and the substance contained in container 138 is to be delivered to the user's oral cavity. An oral orifice element can thus refer to a mouthpiece inserted into the mouth, an earpiece inserted into the tympanic cavity or a nosepiece inserted in one or both of the nostrils. As described below, the inhalation element as an orifice element represents the portion of the replaceable component which is inserted into the user's orifice or cavity, such as the oral cavity, the nasal cavity, and/or the tympanic cavity. Replaceable component 104 can optionally include a heater 140. Output acoustic waveguide 132 is coupled with acoustic signal opening 126, input acoustic waveguide 134 is coupled with reflection signal opening 128 and delivery tube 136 is coupled between container 138 and inhalation opening 130. Container 138 is optionally coupled with heater 140. When replaceable component 104 is attached to and physically coupled with inhalation device 102, power supply 114 can be coupled with heater 140, output acoustic waveguide 132 is coupled with acoustic wave generator 108 and input acoustic waveguide 134 is coupled with acoustic wave sensor 110.

Inhalation device 102 as shown is a reusable device whereas replaceable component 104 is designed to be replaced after use (either one-time use or short-term use). Replaceable component 104 can also be referred to as a cartridge, a pod, a capsule, a disposable and similar terms used to describe one-time as well as short term use items. Whereas FIG. 1 shows inhalation device 102 and replaceable component 104 as separate elements, other configurations of the elements are possible, as described below in FIGS. 2A-2C. Inhalation system 100 can be embodied as any known inhalation device such as an e-cigarette, a vaporizer, a vaping device, a dry herb vaporizer and an inhaler.

Inhalation systems in general are used to deliver a substance to a user as a vapor (gas phase of a substance below its critical point) and/or an aerosol (a colloidal suspension of tiny liquid and/or solid particles in a gas). In this regard, inhalation device 102 represents the reusable part of the system whereas replaceable component 104 represents the cartridge, capsule or pod containing the substance (or a derivate of it) which is to be delivered to a user via inhalation. As shown in FIG. 1, the substance is contained in container 138 from which it is delivered via delivery tube 136 through inhalation opening 130 to a user. The substance can be, for example, nicotine, tobacco, cannabis, a cannabinoid, a liquid containing a cannabinoid, a pharmaceutical substance, an opioid, an opiate, a liquid containing an opioid, a liquid containing an opiate, a liquid containing nicotine and a liquid containing a pharmaceutical substance. The substance can also be an isolated substance, a purified substance, a synthetic substance as well as a substance included in a source material. In an embodiment, a plurality of substances is delivered simultaneously and/or in sequence. The delivered substance to the user may be merely a vapor or an aerosol of the actual substance, such as salbutomal in the case of inhalers which is contained in the container as a liquid and delivered as an aerosol. The delivered substance to the user may also be a vapor or aerosol of a derivative of the actual substance, such as THC acid which is contained within a cannabis leaf but when heated is chemically modified to THC. The substance may also be a mixture. In this respect, a cannabis leaf with THC acid, or isolated or purified THC acid, is a substance contained in the container, however the substance delivered to the user is either THC (with no THC acid) or a mixture of both (depending on the efficiency of decarboxylation). In an embodiment, a plurality of substances is included in the substance and delivered concomitantly and/or in sequence to the user. Thus according to the disclosed technique, inhalation system 100 can deliver a substance as an aerosol or vapor even in the case where the substance contained in container 138 is not a liquid, such as a botanical or a plant material, such as tobacco or cannabis.

Acoustic wave generator 108 can be embodied as any kind of generator that can generate acoustic waves, meaning sound waves which are audible, generally in the range of 20 Hz to 20 KHz. Examples of acoustic wave generator 108 can include a speaker, a tone generator, a buzzer as well as a signal generator having a modulator in a pre-determined frequency range. Acoustic wave sensor 110 can be embodied as any kind of sensor that can sense and detect audible sound waves, such as a microphone and a receiver having a modulator in a pre-determined frequency range. Both of acoustic wave generator 108 and acoustic wave sensor 110 should be sufficiently strong in structure in order to remain resilient under the constant pressure experienced by replaceable component 104 and inhalation device 102 as a user inhales during use of inhalation system 100. Acoustic wave sensor 110 can be embodied, for example, as a ski-slope type microphone which can aid in reducing receiver compression, especially if the acoustic signal transmitted by acoustic wave generator 108 has a low frequency (in the range of 20 Hz to 1.5 KHz), as such microphones have built-in mechanical filters for low frequency signals.

Processor 112 may include an on-board memory (not shown). Processor 112 may include an internal or external acoustical codec unit (not shown). The acoustical codec unit enables processor 112 to use and control analog as well as digital acoustical elements (such as acoustic wave generator 108 and acoustic wave sensor 110). As mentioned above, memory 116 is an optional component and may be included in inhalation device 102 as a separate component (as shown), as an integrated component in processor 112, or as a virtual component in a cloud, cloud server or other computer system (not shown). In the case of the memory being a virtual component, inhalation device 102 may include a wireless transceiver (not shown) for enabling processor 112 to communicate with the memory wirelessly. In general, as described below, the oral signature (either for the purposes of ID or AV) needs to be retrievable from a memory, whether the memory is internal to inhalation system 100 or external to inhalation system 100 but nonetheless accessible.

Actuator 118 schematically represents any kind of button, switch, slide wheel, joystick or similar element that may optionally be used to actuate an element in inhalation device 102. In an embodiment, actuator 118 may be a button, which when pressed, actuates processor 112 to send a signal to acoustic wave generator 108 to generate an acoustic signal. Actuator 118 could also be a switch used to turn power supply 114 on and off. In an embodiment, actuator 118 may be controlled by processor 112 to actuate an element responsible for the delivery of the substance contained in container 138. For example, actuator 118 may be a moveable component which applies a pressure to container 138 for delivering the substance (as a liquid) in container 138 as an aerosol to a user. Actuator 118 could also be a switch for enabling power supply 114 to provide energy to heater 140 for heating up.

Sensor 120 may be any kind of sensor which detects that inhalation element 124 has been positioned in an oral cavity and/or that a user is ready to use (or is already using) inhalation device 102. For example, sensor 120 may be a pressure sensor detecting a change in air pressure in delivery tube 136 thereby indicating an onset of inhalation system 100 by a user. Such a pressure sensor may detect a change in airflow rate in delivery tube 136 above a pre-defined threshold. Sensor 120 may be positioned to detect inhalation via the same airway path (i.e., delivery tube 136) as used by container 138 to deliver a substance to the user, for example by being positioned in the airway or otherwise using the airway. Sensor 120 may be a motion sensor, such as an accelerometer, detecting a change in position of inhalation device 102. Thus a sudden change in position followed by a pre-defined period of no movement (for example a period of movement stability) may be used by sensor 120 to determine that inhalation system 100 is ready to be used by a user for inhaling a substance. In an embodiment a combination of several sensors is used and thus sensor 120 schematically represents such a combination of a plurality of sensors. User interface 122 can be any known user interface to convey information, data, functions and/or states of inhalation system 100 to a user. For example, user interface 122 can be any known surface capable of displaying information to a user and can be embodied as a surface either with or without touch sensitivity. User interface 122 can alternatively be embodied as a variety of sounds and/or lights and can optionally also include a display. In an embodiment of the disclosed technique the user interface may employ acoustic wave generator 108 to transmit sound to the user and/or acoustic wave sensor 110 to receive input from the user. In an embodiment of the disclosed technique, the actuator may be embodied as part of user interface 122 when user interface 122 is a display with touch sensitivity. Power supply 114 may be a rechargeable power supply, such as a lithium ion battery, a nickel cadmium battery and the like. Power supply 114 can also be embodied as a regular battery (i.e., non-rechargeable) or as a power supply coupled to a permanent power source (such as a wall socket or via a USB cable coupled to a device coupled directly with a wall socket such as a computer).

The elements in FIG. 1 are not drawn to scale and are shown schematically to show the coupling and functioning of the elements of inhalation system 100. Acoustic signal opening 126, reflection signal opening 128 and inhalation opening 130 are substantially holes in inhalation element 124. Container 138 is shown as an element within replaceable component 104 however container 138 may actually occupying a significant portion of the volume of replaceable component 104 and delivery tube 136 may be an empty space or hollow in the shape of a cylinder within container 138 and not an actual tube added to replaceable component 104. Acoustic signal opening 126 and reflection signal opening 128 may each be covered by a membrane (not shown) for preventing dirt, dust and debris (and even liquid) from entering acoustic signal opening 126 and reflection signal opening 128. A proximal end 133 of output acoustic waveguide 132 as well as a proximal end 135 of input acoustic waveguide 134 may be open and are each configured to be coupled respectively with acoustic wave generator 108 and acoustic wave sensor 110 when replaceable component 104 is attached to inhalation device 102. Output acoustic waveguide 132 and input acoustic waveguide 134, similar to delivery tube 136 may be embodied as empty spaces or hollows, optionally in the shape of a cylinder within container 138 and may not be actual tubes added to replaceable component 104. Proximal ends 133 and 135 may be acoustically sealed respectively with acoustic wave generator 108 and acoustic wave sensor 110 when replaceable component 104 is attached to inhalation device 102. Proximal ends 133 and 135 may insert into an acoustic seal (not shown) in acoustic wave generator 108 and acoustic wave sensor 110. The acoustic seal may be a hermetic seal such that no air enters proximal ends 133 and 135 once they are respectively coupled to inhalation device 102. The acoustic seal can be made from any relatively elastic material that deforms under slight pressure and will change shape to fill gaps between proximal ends 133 and 135 and acoustic wave generator 108 and acoustic wave sensor 110 thereby preventing the entry of air from proximal ends 133 and 135 when attached to inhalation device 102. The elastic material should be flexible and dense, such as silicone or rubber. Examples of the acoustic seal are shown below, for example in FIGS. 7A-7B and 9. The acoustic seal can also be embodied a ring made of an elastic material, optionally silicone or rubber, placed around an entry point (not shown) in acoustic wave generator 108 and acoustic wave sensor 110 where proximal ends 133 and 135 are inserted into.

Heater 140 is an optional component and may only be present in replaceable component 104 in the case of a substance in container 138 which can be heated in order to be delivered to the user via inhalation opening 130. In the case of the substance in container 138 being a liquid which is turned into an aerosol to be delivered to the user, heater 140 is not included in inhalation system 100. Heater 140 may be a heating element, a filament, a wire or any other structure which emits heat when energy is applied to it. In the embodiment where heater 140 is included, when replaceable component 104 is attached to inhalation device 102, heater 140 may be electrically coupled with power supply 114 such that energy can be provided from power supply 114 to heater 140 which can then in turn provide heat to container 138 for heating the substance contained therein.

According to an embodiment of the disclosed technique, inhalation system 100 generally works as follows. Replaceable component 104 is inserted and attached to inhalation device 102. Inhalation element 124 is then positioned in a user's oral cavity. As mentioned above, an embodiment of actuator 118 may be used to indicate to processor 112 that the user is ready to use inhalation system 100 or an embodiment of sensor 120 may be used to detect that inhalation element 124 has been positioned in the user's oral cavity. Optionally, sensor 120 is used to indicate that inhalation has commenced. Optionally, transmission of acoustic signals to the user's oral cavity is timed according to the inhalation of the user and thus transmission is timed to commence at a specific point in time during one or more inhalations of the user, for example once a pattern of airflow rate is detected, for example by sensor 120, or a pre-defined period of time has passed from detecting the onset of inhalation of the user. Processor 112 sends a command to acoustic wave generator to generate an acoustic signal, graphically shown as acoustic signal 142, which travels through output acoustic waveguide 132 and exits acoustic signal opening 126 into the oral cavity of the user. Reflections from acoustic signal 142 within the oral cavity are received via reflection signal opening 128 which then guides the reflected acoustic signal, graphically shown as reflected signal 144, towards acoustic wave sensor 110 which detects properties of reflected signal 144, such as its amplitude and frequency. The acoustic signal sent to the oral cavity and received as reflections is referred to as an oral sample, as mentioned above. Acoustic signal 142 may be a plurality of signals and reflected signal 144 may be a plurality of reflected signals, as described below in further detail. The detected properties of reflected signal 144 are passed from acoustic wave sensor to processor 112 for analysis.

In an embodiment, processor 112 and/or memory 116, stores an oral signature of the user, which substantially includes the properties of a reflected signal to a user's oral cavity. In an embodiment, processor 112, and/or memory 116, stores an oral signature containing features for a group of users defined by an age limit or age group. These oral signatures and their corresponding features are further detailed below. Processor 112 compares reflected signal 144 to the stored oral signature of the user or the features of the oral signature of the group. As mentioned above, the oral signature or the features of an oral signature are retrievable by processor 112 in order to compare it to reflected signal 144.

If reflected signal 144 is similar enough (for example being above a given threshold) to the stored oral signature or features of an oral signature, processor 112 then gives a command to deliver the substance in container 138 to the user via delivery tube 136. Processor 112 can optionally give a command to control other elements in inhalation system 100, such as a valve (not shown) or an actuator for directing the substance in container 138 to the user. For example, the command may be given to at least one of container 138, actuator 118, heater 140 and power supply 114. As shown, the substance is delivered to the user's oral cavity as a vapor or aerosol, graphically shown as delivered substance 146, via delivery tube 136 through inhalation opening 130.

The threshold for similarity may be a fixed value or may be adjustable, for example, according to the substance being delivered. For example, in a device capable of delivering a recreational substance (e.g., tobacco) and a controlled substance (e.g., medication, such as an opiate), the settings for each substance may include a corresponding threshold. In the event that the probability of false negatives is reduced (for example due to repeat uses, as exemplified below), the threshold may adjust automatically to a higher value.

As described below, reflected signal 144 (i.e., the oral sample) and the stored oral signature and/or signature features are considered similar enough when the probability that reflected signal 114 is the same as the oral signature is above a pre-defined threshold. If the reflected signal is found to be similar enough, then it can be said that the user has been authenticated. In an embodiment, processor 112 gives an indication to enable the substance in container 138 to be delivered to the user upon authentication. In an embodiment, depending on the type of substance in container 138, the indication can cause a signal to be sent to heater 140 to heat the substance in container 138 or to cause actuator 118 to release pressurized air in container 138 to deliver the substance as a vapor or an aerosol. If the reflected signal is not found to be similar enough, then the user is not authenticated. Processor 112 may then provide no indication, or processor 112 might provide an indication that the user was not authenticated (for example, via user interface 122) and thus no further signal is provided to deliver the substance in container 138 to the user. In an embodiment, upon indication that the user was not authenticated, processor 112 may block, deactivate and/or limit the substance delivery of the inhalation system. It is noted as well that in the case of AV, the authentication of a user's sample may also be used to verify a user's age or age group and accordingly an authentication may also be used to block, deactivate and/or limit the use of inhalation system 100. For example, if the cavity sample sufficiently matches the stored oral signature features of a non-permitted user (such as a minor trying to use an embodiment of the disclosed technique as a vaping device), the user may be authenticated as a non-permitted user. In an embodiment of the disclosed technique, AV authorization requires two levels of authentication, one level in which the cavity sample sufficiently matches the stored oral signature features of a permitted user and a second level in which the cavity sample dose not sufficiently match the stored oral signature features of a non-permitted user.

As mentioned above, the disclosed technique provides methods and systems for authentication of an electronic device for use in a human cavity having low latency. Part of the desire for low latency can be to enhance the user's experience when using the disclosed technique. For example, with regards to inhalation system 100 embodied as an e-cigarette or a vaping device, the entire process for authenticating a user and then delivering the substance in container 138 to the user's oral cavity should generally occur within a time duration similar to the process of providing the substance in the container in a conventional e-cigarette or vaping device. For example, the action of using an inhalation system such as an e-cigarette or vaping device can be referred to as taking a puff, which might last between 1-3.5 seconds. Thus, according to the disclosed technique, the entire process for authenticating a user and then delivering the substance in the container to the user should be completed within the time period of a single puff. According to the disclosed technique, the process for authenticating a user can take approximately 500 milliseconds (herein abbreviated msec) and may be as short as 300 msec, thereby not affecting the user experience of inhalation system 100 as compared to conventional e-cigarettes and vaping devices. Authentication can also occur during use of inhalation system 100, for example 350 msec before the substance is released, delivered and/or before access to the substance is granted. Authentication can continue and/or be repeated before the end of substance delivery as a condition for continued use. Inhalation system 100 may prevent further use if a second oral sample during use is not authenticated and/or does not correlate with sufficient similarity to the first, or a previous oral sample taken. Inhalation system 100 may prevent further use by comparing all previous oral samples taken during an inhalation or a pre-defined number of inhalations. In another example, a medical substance inhaler can sometimes require an inhalation of 1-3 seconds or longer for drug delivery. According an embodiment of the disclosed technique wherein drug delivery can only commence after successful user authentication, the entire authentication process should be short enough to accommodate even frail patients, for example not exceeding 350 or 400 msec to be followed with drug delivery in the same inhalation. In an embodiment where the substance to be delivered is a recreational substance or over-the-counter medication which does not requiring any special permission (such as a doctor's prescription), substance delivery may commence before authentication is complete, in which case the authentication may at least partially overlap with substance delivery.

As mentioned above, according to the disclosed technique, authentication of a user can occur in one of two general types of authentication, ID (identification verification) in which an individual is identified by their cavity signature as stored in inhalation device 102 or AV (age verification) in which an individual is identified as belonging to a category of permitted users, optionally based on age, in which the features of a cavity signature of a permitted user are stored in inhalation device 102. In the context of AV, the features of a permitted user are not the features of a specific individual but rather features that are useful in identifying permitted users as well as non-permitted users.

The nature of the structure of human cavities such as the oral cavity, the nasal cavity and the tympanic cavity is generally considered a unique and distinct biometric identifier, even amongst identical twins, similar to the variable nature of the structure of the retina, facial features as well as fingerprints. Taking the oral cavity as an example, the position and size of the teeth, the size of the actual oral cavity, the particular shape of the jaw and other features of the oral cavity partially defined by a person's genetics, provide the oral cavity of a user with a unique 'signature' that can be categorized using acoustic signals. The anatomical differences listed above and/or other features (discernable using acoustic signals) are such that acoustic signals transmitted to the oral cavity of a user will reflect with a unique frequency response which can be used to establish an oral cavity signature. In addition, due to the physiological differences between children, adolescents and adults regarding physical size and tissue structure, features of an oral cavity signature can be discerned, according to the disclosed technique and as described below, based on the age (or age group) of the user. Thus, features of permitted users as well as non-permitted users based on an oral signature can be discerned and used to identify for example whether a user is a child, an adolescent or an adult above a specified age.

Whereas a model of the oral cavity of a user may be built using signals of any kind, including electromagnetic signals, such as in the case of MRI scanning or PT scanning, the disclosed technique provides for a model of a user's oral cavity using acoustic signals and generating an oral signature within a time frame that is on the order of the time required to take a single puff or inhalation in an inhalation system. A number of constraints exist in generating a cavity signature in general, and in the case of inhalation system 100 an oral signature in particular, within the aforementioned time constraints, which might last as long as a few seconds however might be as short as 350 msec or even shorter in duration. A first constraint is the quality of the acoustic signal transmitted to the oral cavity. Acoustic signals having a low SNR may not yield sufficient discernable features in the reflected signal to accurately authenticate a user. A second constraint is the intensity of the acoustic signal transmitted to the oral cavity. On one limit, ambient noise may be present in the oral cavity whereas on the other limit, excessively intense acoustic signals may reduce a user's experience of the disclosed technique or possibly cause damage. Sufficiently intense acoustic signals may be heard by a person other than the user, thus potentially affecting the user's ability to use (and enjoy) the device in public. A third constraint is the variance in frequency response of an acoustic signal. The transmitted acoustic signal can be such that the frequency response of the reflected signal has sufficient variance in terms of discernable features to increase the probability that the frequency response of a reflected signal of a given user is indeed unique and personal, for example in the case of ID. The variance constraint also applies in the case of AV, wherein the frequency response of the reflected signal for a group of users, for example based on age, should be sufficiently different between age groups such that features can be discerned so as to differentiate different age groups (such as child, adolescent and adult).

According to the disclosed technique, an authentication process within the aforementioned time constraints potentially provides enhanced protection and security features for an inhalation device and other devices useable with the disclosed technique. A sufficiently fast authentication process (for example, on the order of a few hundred milliseconds) can enable authentication of a user to be repeated each time she takes a puff, thus preventing a user from beating, cheating or manipulating the authentication process even if attempted willingly. Thus a user cannot take a puff and then pass the inhalation device to either a non-permitted user (in the case of AV) or non-registered user (in the case of ID), either willingly or unwillingly, who may have assumed that once a single authentication instance has occurred (for example in the case of entering a password or having a fingerprint scanned), access to the inhalation device is readily available. The disclosed technique provides for ongoing low latency authentication to ensure that only a registered and/or permitted user uses the inhalation device. Another potential benefit of a sufficiently fast authentication process according to the disclosed technique is to keep the time duration between authentication and the delivery of a substance sufficiently short to prevent a user authenticating herself and then transferring the inhalation device quickly to another user, either non-registered or non-permitted, to inhale the substance. It is noted that in such an instance, other methods can be used according to the disclosed technique to prevent cheating or beating the authentication process, such as sensing a break period in inhalation, or using a sensor, such as sensor 120, for detecting excessive motion of inhalation system 100, and thereby resetting the entire authentication process. Yet another potential benefit of a sufficiently fast authentication process according to the disclosed technique is that a delay in substance delivery that is due to the authentication process is short enough so as not be noticeable to the average user.

According to an embodiment of the disclosed technique, the properties and parameters regarding the acoustic signals which satisfy the aforementioned criteria are as described herein. According to the disclosed technique, acoustic wave generator 108 can generate an acoustic signal within the audible range of 20 Hz to 20 KHz, however acoustic signals in the range of 1.5 KHz to 9 KHz and more so acoustic signals in the range of 1.5 KHz to 5 KHz have been found to provide a more varied frequency response amongst different users and amongst different ages of users. As mentioned above as well, depending on the human cavity in which the disclosed technique is used, the acoustic signal may have a range of 9 KHz to 20 KHz, 20 Hz to 1.5 KHz or even 20 Hz to 9 KHz.

The acoustic signal transmitted by acoustic wave generator 108 may thus be a sweep signal, such as a chirp signal, in which acoustic waves having different frequencies are transmitted within a transmission window. For example, acoustic wave generator 108 may transmit a sweep signal having a continuous frequency range of 1.5 KHz to 9 KHz. The sweep signal does not need to cover the entire aforementioned range and can have a range which is a subset of the aforementioned range, for example, from 1.5 KHz to 5 KHz, 3 KHz to 6 KHz or from 4.5 KHz to 8.5 KHz. The sweep signal can also have a non-continuous range of frequencies within a single signal, such as from 1.5 KHz to 3 KHz and 5 KHz to 9 KHz. As mentioned, acoustic wave generator 108 may transmit more than one acoustic signal to obtain a sample of the frequency response of a user's oral cavity. Acoustic wave generator 108 may transmit a plurality of acoustic signals within a single transmission window. Acoustic wave generator 108 may also transmit a plurality of acoustic signals within a plurality of transmission windows. Thus sweep signals having different frequency ranges may be transmitted, such as a first sweep signal having a frequency range of 1.5 KHz to 3 KHz, a second sweep signal having a frequency range of 5 KHz to 6 KHz and a third sweep signal having a frequency range of 7.5 KHz to 8.5 KHz. The three aforementioned sweep signals may be transmitted in succession within a single transmission window or across a plurality of transmission windows. Alternatively, sweep signals having different non-continuous ranges can also be transmitted, such as a first sweep signal having a frequency range of 5 KHz to 6 KHz and 8 KHz to 9 KHz and a second sweep signal having a frequency range of 1.5 KHz to 3 KHz and 7 KHz to 9 KHz.

In addition, according to the disclosed technique, waveguides (such as output acoustic waveguide 132 and input acoustic waveguide 134) are used between acoustic wave generator 108 and acoustic signal opening 126 and reflection signal opening 128 and acoustic wave sensor 110 to increase the SNR of acoustic signal 142 as transmitted to a user's oral cavity as well as the SNR of reflected signal 144 as received by acoustic wave sensor 110. The length of output acoustic waveguide 132 and input acoustic waveguide 134 as well as the distance between them (in particular the distance between acoustic signal opening 126 and reflection signal opening 128) can influence the SNR of acoustic signal 142 as well as reflected signal 144. As inhalation system 100 is used by insertion into a user's oral cavity, the distance between acoustic signal opening 126 and reflection signal opening 128 is limited by the size of a user's mouth. However as the distance between acoustic signal opening 126 and reflection signal opening 128 is reduced, the probability of interference between acoustic signal 142 and reflected signal 144 in the user's oral cavity increases, as a larger portion of acoustic signal 142 might enter reflection signal opening 128 directly before impinging upon the inner surface of the user's oral cavity and reflecting back towards reflection signal opening 128. In addition, as acoustic signals attenuate significantly even over short distances, the length of output acoustic waveguide 132 and input acoustic waveguide 134 determines the general intensity (and thus associated volume) of acoustic signal 142 to be transmitted. As mentioned above, according to the disclosed technique, the intensity of acoustic signal 142 needs to be balanced between being substantially higher than any ambient noise coming from the user's oral cavity however an intensity which is too high will result in receiver compression of reflected signal 144 in acoustic wave sensor 110 when reflected signal 144 is received. Each of the above constraints can have a direct effect on the SNR of both acoustic signal 142 and reflected signal 144.

According to an embodiment of the disclosed technique, acoustic signal opening 126 and reflection signal opening 128 should have a minimal distance gap, as shown by a distance 148, to reduce the effects of interference between acoustic signal 142 and reflected signal 144 and the direct transmission of acoustic signal 142 to reflection signal opening 128. Distance 148 defines the system sensitivity, wherein a shorter distance between the openings reduces sensitivity. Thus, the minimal distance gap is large enough so as to reduce the power of any direct transmission of acoustic signal 142 via acoustic signal opening 126 to reflection signal opening 128. On the other hand, the length of distance 148 is limited according to cavity size. The minimal distance gap can range from mm up to 25 mm. The maximum distance gap can be between 1 cm and up to 3 cm. For example, distance 148 could be 12 mm. In general, distance 148 can be as large as possible within the above limitations as the inventors have discovered that this increases the sensitivity of acoustic wave sensor 110 and thus its ability to discern more features from reflected signal 144. As shown in FIG. 1, output acoustic waveguide 132 and input acoustic waveguide 134 are schematically drawn as being identical in shape and size, however output acoustic waveguide 132 and input acoustic waveguide 134 can have different sizes, shapes and lengths and do not need to be the same. Optionally output acoustic waveguide 132 and input acoustic waveguide 134 are not aligned, for example at their distal end (i.e., the end proximal to the user's cavity, when in use). Thus, output acoustic waveguide 132 may extend further into the user's mouth than input acoustic waveguide 134. Output acoustic waveguide 132 and input acoustic waveguide 134 can have a length ranging from 10 mm to 50 mm. Output acoustic waveguide 132 and input acoustic waveguide 134 can also have even shorter lengths, for example being as short as 1-2 mm. Output acoustic waveguide 132 and input acoustic waveguide 134 can be made from metal, plastic or silicone. Each material may affect the power efficiency of the transmitted acoustic signal and the received acoustic signal differently and is thus a design choice depending on the use of the disclosed technique, optionally including consideration of power usage and user experience. Output acoustic waveguide 132 and input acoustic waveguide 134 can have a diameter which is either constant along its length or varies along its length. For example, proximal ends 133 and 135 may have a smaller diameter than the distal ends (not labeled) of output acoustic waveguide 132 and input acoustic waveguide 134 which couple with acoustic signal opening 126 and reflection signal opening 128, thereby giving output acoustic waveguide 132 and input acoustic waveguide 134 a tapered shape. Having the distal ends of the waveguides with a larger diameter increases the spread of acoustic signal 142 within the oral cavity while also increasing the amount of reflected signal 144 which enters reflection signal opening 128. As an example, output acoustic waveguide 132 and input acoustic waveguide 134 may each have a length of 30 mm, having a diameter of 1.5 mm at their proximal ends and increasing to a diameter of 2.5 mm at their distal ends. The waveguides shown in FIG. 1 are shown as being straight between their proximal and distal ends, however the waveguides of the disclosed technique can be curved or follow other shaped paths from their proximal end to their distal end. The length and shape of output acoustic waveguide 132 and input acoustic waveguide 134 can influence the size of container 138. As mentioned above and shown below, container 138 may occupy a significant portion of replaceable component 104, wherein container 138 contains the substance to be delivered. Thus, minimizing the size of the waveguides enables maximizing the size of container 138 and thus the amount of substance which container 138 can hold. It is noted that the materials from which output acoustic waveguide 132 and input acoustic waveguide 134 are made can be different than the material from which delivery tube 136 is made. The materials used for the waveguides may be selected to be materials which will not affect the acoustic signal (for example, changing any characteristics of the acoustic signal) as it travels through the waveguide. Delivery tube 136 on the other hand may be made of a material that will not absorb and/or will not increase condensation on the walls of the delivery tube as it travels from container 138 towards inhalation opening 130 towards a user's mouth. As mentioned above, output acoustic waveguide 132 and input acoustic waveguide 134 may have significantly different sizes and dimensions, and the sizes and dimensions of the waveguides may be different than the size and dimension of delivery tube 136. For example, one or more of the waveguides may be narrower to allow increasing the volume of container 138 without affecting the width of the mouthpiece and/or to allow reducing the total size of replaceable component 104 and/or of inhalation element 124 whereas delivery tube 136 may be wider, for example to reduce the waveguide surface/volume ratio thereby reducing substance condensation on the tube walls and/or to allow for the substance to be inhaled faster through inhalation opening 130.

An additional consideration according to the disclosed technique includes the shape of both the proximal and distal ends of output acoustic waveguide 132 and input acoustic waveguide 134, the shape of the waveguides themselves as well as the shape of acoustic signal opening 126 and reflection signal opening 128. Whereas the shape of the proximal and distal ends of output acoustic waveguide 132 and input acoustic waveguide 134 and of acoustic signal opening 126 and reflection signal opening 128 can be round, with the overall shape of the waveguides being cylindrical (and thus being circular or ovular in cross-section), other shapes are possible according to the disclosed technique, such as a square or rectangular shape for the proximal and distal ends of the waveguides, as well as a D-shape for acoustic signal opening 126 and reflection signal opening 128. The shape and size of acoustic signal opening 126 and reflection signal opening 128 may respectively aid in directing acoustic signal 142 towards the user's cavity and receiving and directing reflections of acoustic signal 142 as reflected signal 144 towards acoustic wave sensor 110. The shape and size of acoustic signal opening 126 and reflection signal opening 128 may also enable acoustic signal 142 to be conveyed within the used frequency range (for example 1.5 KHz to 9 KHZ). The waveguides may also have a different overall shape, for example having a cross-section which is triangular, pentagonal or square. According to the disclosed technique, the size of acoustic signal opening 126 and reflection signal opening 128 is to be balanced such that sufficient acoustic energy is transmitted as acoustic signal 142 and received as reflected signal 144 yet also not being too large, so as to avoid the entry of dirt, debris, dust and even liquids within output acoustic waveguide 132 and input acoustic waveguide 134. As mentioned above, acoustic signal opening 126 and reflection signal opening 128 may both be covered by a membrane, thereby enabling acoustic waves to pass there through but preventing the entry of foreign objects and particles into the waveguides. The membrane may be a foil of sorts and can be transparent. According to the disclosed technique, proximal ends 133 and 135 are acoustically sealed with acoustic wave generator 108 and acoustic wave sensor 110, respectively. When replaceable component 104 is inserted into and attached with inhalation device 102 there is generally no (i.e., zero) air gap between the wave generator and wave sensor and their respective waveguides. If there is an air gap present, then the insertion of replaceable component 104 into inhalation device 102 is such that the air gap itself provides acoustic sealing or that the airgap is not significant enough to interfere with the acoustic sealing.

As mentioned above, inhalation element 124, which is positioned in the user's oral cavity (for example their mouth), or at least a part thereof, should be made from a material having sufficient surface hardness to afford sufficient acoustic isolation when a user closes their mouth over inhalation element 124. The material should also be sufficiently rigid thus preventing any deformation to output acoustic waveguide 132 and input acoustic waveguide 134 when inserted into a user's oral cavity and gripped by the user's lips and/or teeth. As different materials have different acoustic properties, the material selected for inhalation element 124 and/or replaceable component 104 should be selected such that it provides good acoustic sealing (i.e., sound attenuation) for sound travelling in air. Some materials, such as silicone, may not provide such properties. As inhalation element 124 is positioned inside a person's mouth, the material it is made from should also be biocompatible, such as polypropylene, polycarbonate, acrylonitrile butadiene styrene (ABS), polyamides such as nylon, polyethylene, and the like. In general, replaceable component 104 may be made from a similar material as inhalation element 124, however any solid material can be used, such as a solid plastic. The general material of replaceable component 104 or some parts thereof can also be biocompatible, since some or all of the parts of replaceable component 104 might enter the user's mouth. The same applies to any surface in replaceable component 104 that can come in contact with the substance, and thus should be biocompatible for safety and health reasons. In an embodiment, elastic materials such as silicon and rubber should not be used for either inhalation element 124 or for replaceable component 104 as the soft texture of such materials may interfere with the transmitted and reflected acoustic signals which are significant to the characterization of the oral signature or oral sample. Elastic materials may also not support the shape of the waveguides, especially over long term use. Elastic materials may also deform over time, thus causing a change in acoustic signal 142 and reflected signal 144. Nonetheless, some parts of either inhalation element 124 or replaceable component 104 may comprise such elastic materials. For example, silicone may cover a rigid component, whereby the silicone may provide a pleasant touch sensation and/or assist in acoustically sealing the user's mouth over inhalation element 124 while an internal rigid portion would provide the required prevention of deformation. The material(s) from which replaceable component 104 and inhalation element 124 are made should provide sufficient mechanical strength to contain the substance in container 138 even under pressure when a user grips inhalation element 124 with their teeth and/or lips. In an embodiment, at least one of replaceable component 104, container 138 and inhalation element 124, or any part thereof, may be made from a transparent material so the contents of container 138 are visible, for example if container 138 contains a fluid, the amount of fluid remaining can be gauged.

As an embodiment of the disclosed technique relate to an inhalation system, wherein it is reasonably assumed that a user inhaling a substance wants to maximize the inhalation of the substance and thus will cover the inhalation element with their mouth as best they can to avoid any of the substance escaping to the air and not entering their body, it can thus be assumed that the user will create an acoustic seal with their mouth around inhalation element 124 when inserted into their mouth provided inhalation element 124 is made from a material as stated above. According to the disclosed technique, the size and shape of inhalation element 124 may be configured and designed to enhance user comfort as well as the sensitivity of inhalation device 102. For example, inhalation element 124 may be rounded or ovular to resemble the general shape of the mouth as opposed to being flat or square (even though such shapes are also possible). Such shapes also increase the sensitivity of inhalation device 102 by improving the general acoustic seal the user makes with inhalation element 124 with their mouth when it is inserted into their mouth. Inhalation element 124 may include grooves, markings, indentations (all not shown) and the like for either the lips, teeth and/or tongue of the user as a placement marker for proper positioning of inhalation element 124 in the mouth of the user. Such placement markers can reduce or prevent the interference of the user's lips, tongue and teeth with acoustic signal opening 126 and reflection signal opening 128 which can influence the SNR of acoustic signal 142 and reflected signal 144. Thus in general, inhalation element 124 may be in direct contact with a user's mouth (or another cavity of the user), however in an embodiment, acoustic signal opening 126 and reflection signal opening 128 are not in direct contact with any surface of the user's body so that acoustic signals which are transmitted and received are not affected or altered based on direct contact with the body.

As mentioned above, the size and shape constraints of the waveguides, as well as the ambient noise in the user's mouth, influences the parameters of acoustic signal 142, in which it is desired to achieve maximum SNR while also avoiding any receiver compression in acoustic wave sensor 110. Acoustic wave generator 108 may be able to produce acoustic wave signals having a maximum volume of approximately 90 decibels (herein abbreviated dB) (which is around 20 dB SPL). As mentioned above, since acoustic waves attenuate significantly over distance, the length of the waveguides will determine the actual volume acoustic wave generator 108 transmits acoustic signal 142 in a given implementation of the disclosed technique. The upper limit of the volume of acoustic signal 142 can be below an intensity threshold so that when reflected signal 144 is received at acoustic wave sensor 110, receiver compression is not generated in the wave sensor. The lower limit of the volume of acoustic signal 142 can be sufficiently above ambient noise in the user's oral cavity, which in general is the ambient noise of the user's own breathing. Also, a lower volume is preferred to enhance the user experience, with the volume of acoustic signal 142 being non-audible at least for a person standing near the user but optionally also for the user themselves. In order to provide such non-audibility, the intensity (i.e., the volume), duration and frequency arrangement of acoustic signal 142 can be balanced in a given implementation of inhalation system 100 based on the constraints listed above, as per the disclosed technique. Herein a few examples of this are given, however it should be noted that these are mere examples, and based on the description above, the worker skilled in the art would be able to determine other configurations of the parameters of acoustic signal 142 based on the parameters of an implementation of inhalation system 100.

In a first example, assuming inhalation element 124 is relatively long, having a depth 149 of 50 mm, and output acoustic waveguide 132 and input acoustic waveguide 134 each have a relatively small circular cross-section (in order to reduce the volume (size) of the waveguides at the expense of the volume (size) of container 138) having a diameter of less than 1.5 mm, acoustic signal 142 and reflected signal 144 will experience high attenuation. The volume (intensity) of acoustic wave generator 108 might thus be increased up to 90 dB relative to 20 dB SPL. Acoustic wave generator 108 may also generate a sweep signal, as acoustic signal 142, having a longer duration (such as 80 msec as compared to 50 msec) if the volume of the sweep signal reaches the volume limit of 90 dB. In addition, the narrow cross-section shape of the waveguides might cause significant attenuation in specific frequency bands in the sweep signal, thus the sweep signal might exclude certain frequency bands. For example, acoustic signal 142 may be a sweep signal having a frequency range of 1.5-3 KHz and 5-9 KHz, however 3-5 KHz will be excluded from the sweep signal. Given the reduction in the frequency range of acoustic signal 142, the sensitivity of acoustic wave sensor 110 may be increased to enable an increase in amplification of reflected signal 144.

In a second example, assuming inhalation element 124 is of relatively medium length, having depth 149 of 30 mm, and output acoustic waveguide 132 and input acoustic waveguide 134 each having a relatively medium circular cross-section having a diameter of between 1.5 mm to 2.5 mm (as the shorter length of the inhalation element and thus shorter length of the waveguides allow for an increase in diameter while maintaining the same volume as the volume in the first example), acoustic signal 142 and reflected signal 144 will experience medium attenuation. The volume of acoustic wave generator 108 might thus be increased up to 80 dB relative to 20 dB SPL and acoustic wave generator 108 may generate a sweep signal, as acoustic signal 142, having an average duration of 50 msec. The larger diameter of the waveguides may be sufficient such that there is no significant attenuation in specific frequency bands in the sweep signal and thus the sweep signal may contain all the frequency bands as per the disclosed technique. For example, acoustic signal 142 may be a sweep signal having a frequency range of 1.5-9 KHz.

In a third example, with inhalation element 124 being of relatively short length, having depth 149 of 15 mm, and output acoustic waveguide 132 and input acoustic waveguide 134 each having a relatively large circular cross-section having a diameter of between 2.5 mm to 4 mm, a low attenuation will be experienced by both acoustic signal 142 and reflected signal 144 for all frequency bands in those signals. Thus the volume of acoustic wave generator 108 might thus be increased up to 75 dB relative to 20 dB SPL and acoustic wave generator 108 may generate a sweep signal, as acoustic signal 142, having an average duration of 50 msec with a continuous frequency range of 1.5-5 KHz.

As inhalation system 100 operates using an oral signature, thereby allowing the substance in container 138 to be inhaled only if the user is properly identified, inhalation system 100, and in particular processor 112, requires either a stage of registration prior to first use in the case of ID, or being embedded with a trained sorting algorithm in the case of AV. In general, the process of registration refers to an intake period in which relevant information relating to an individual is recorded. In the case of the disclosed technique, the process of registration involves generating an oral signature of a user which can then be used in future uses of inhalation system 100 to authenticate that a given user is the registered user of inhalation system 100. The registration process of inhalation system 100 may involve the user placing inhalation element 124 in their mouth continuously or intermittently for a registration period of time, for example a minute or a few minutes, wherein a plurality of samples of acoustic signal 142 are transmitted and then received by acoustic wave sensor 110 and analyzed by processor 112. The user may be instructed to position inhalation element 124 in their mouth at various angles and to various depths during the registration process in order to construct a robust oral signature. Such a registration process is similar to voice registration processes for over the phone banking services or facial recognition registration processes for mobile phones. The plurality of samples of acoustic signal 142 may be the acoustic signals having the same properties (volume, frequency range, duration and the like) or having different properties. As users have physiological differences, including the shape and features of their oral cavity, the registration process may take longer or shorter for certain individuals depending on the features which processor 112 can extract from the reflections of the acoustic signals transmitted to the user's oral cavity. The registration process may also include sending acoustic signals in different frequency ranges as the reflections in different users may be more informative in some and less informative in others. For example, more discernible features in reflected signal 144 may be present in the frequency range of 1.5-5 KHz for some users whereas in other users, more discernible features in reflected signal 144 may be present in the frequency range of 3-7 KHz. These ranges are merely examples. The registration process in an embodiment of the disclosed technique may even include taking a few samples of acoustic signals in various frequency ranges to determine which frequency range is most informative of a specific user's oral signature and then registering the oral signature of the user using a frequency range which is specifically more informative for that user. It is noted that inhalation device 102 may use a reference wave to perform an initial calibration between acoustic wave generator 108 and acoustic wave sensor 110. In an embodiment wave sensor 110 will record the ambient sound as a reference prior for the authentication and/or registration process of a user.

User interface 122 may provide instructions to the user regarding the positioning of inhalation element 124 in their mouth as well as to the onset and end of the registration process. This can be accomplished for example via a sequence of lights, sounds and/or images displayed on a display. According to an embodiment of the disclosed technique, once registered, the oral signature of the user may be stored in processor 112 or memory 116, thus locally in inhalation system 100. In an embodiment, the oral signature of a user may be stored in a virtual memory component, such as a cloud storage system and/or in a centralized memory component, such as a computer server of an institution. In an embodiment, the oral signature of the user is stored both internally in inhalation system 100 and also externally in a memory component external to the inhalation system, such as in a cloud storage system. In addition, inhalation system 100 may store a plurality of oral signatures, meaning oral signatures for a plurality of users. Thus, multiple registered users may be able to use a single inhalation system according to the disclosed technique (for example, an inhaler that is being used by a few members of a family, or in a healthcare center). Optionally a user can be registered as a restricted user. For example, a person with a medical inhaler registered to her oral signature may wish to register another individual (such as her child) as a restricted user, thereby decreasing the probability of that other individual using the inhalation system due to a false positive result. It is noted as well that during the registration process, there may be built-in lags between the samples of the acoustic signal in order to perform initial processing of the reflected signal before the next transmission, thus saving on memory space (especially in the case where the memory is internal to the system).

In the case of identification verification, a user can be first registered with inhalation system 100. Once registered, when the user wants to use inhalation system 100, a cavity sample of their oral cavity is taken and compared to the stored and registered oral signature in inhalation system 100. As mentioned above, this sample can be referred to as an oral sample. The oral sample may include a small number of acoustic signals transmitted to their oral cavity and received as reflections in acoustic wave sensor 110 within a pre-defined sampling window. An analysis of the features of the oral sample can then be compared to the stored oral signature and if the features of the oral sample are similar enough to the features of the oral signature, the user's oral sample is said to have been authenticated. Registration and authentication of a user of inhalation system 100 can be executed using a classifier, a machine learning algorithm and the like, such as a gradient boosting algorithm, the light gradient boosted machine (LightGBM) algorithm, the XGBoost algorithm, as well as Neutral Network package in R or any specially designed Neural Network in any known implementation language. A more detailed explanation of the procedures of registering and authenticating users according to the disclosed technique is described below in FIGS. 11 and 12.

According to the disclosed technique, an oral sample can be taken every time the user uses inhalation system 100 and inhales to administer the substance in container 138. The oral sample can be taken a number of times when the user initially begins using inhalation system 100 in order to establish that the user is indeed a registered user. In an embodiment, an oral sample can be taken once in a pre-defined time period, such as one every 5 minutes and/or once per usage number, such as once every 10 puffs. In an embodiment an oral sample is taken for each inhalation of the user. In an embodiment an oral sample is taken during substance delivery, with authentication of the user being completed before drug delivery. In an embodiment an oral sample is taken during a period of time that at least partially overlaps with substance delivery, with the user authenticated being completed before drug delivery, thereby optionally terminating delivery before completion and/or issuing a signal reporting unauthorized use. Optionally, authentication of the oral sample is a condition for both commencement of delivery of the substance and continual delivery of the substance during a single inhalation. In an embodiment, authentication is performed more than once during a single inhalation, such as once before drug delivery begins and at least once more during delivery. A later authentication may use an oral sample taken specifically for the later authentication and/or combine the oral samples of one or more previous authentications.

The process of authenticating an oral sample as well as then delivering the substance in container 138 to the user (including possibly heating up the substance) can take place within the normative amount of time during which a user may inhale via inhalation system 100. A user may inhale inhalation system 100 quickly, for example within a few hundred milliseconds, or may take a long draw and inhale for a few seconds. According to the disclosed technique, the process of authenticating a user's oral sample, heating up the substance in container 138 (if required) and delivering the substance in container 138 as a vapor or aerosol may be completed within 1-3.5 seconds or within 0.5-5 seconds. According to the disclosed technique, the process of authenticating the user's oral sample may be completed within 500 msec and in an embodiment, within 350 msec, which is generally a time period not discernable by humans. According to the disclosed technique, an oral sample may include a plurality of acoustic signals, for example, 3 sweep signals having a duration of 50 msec each, with a short time gap between each sweep signal (for example 20 msec). Each reflected signal 144 from the 3 sweep signals may thus be received in acoustic wave sensor 110 in around 200 msec and then analyzed in processor 112 in around 150 msec. However, the sweep signal itself may last anywhere between msec with a gap lasting anywhere between 5-100 msec. Thus an oral sample could range from lasting 10 msec if a single sweep signal of msec is used up until 500 msec if 10 sweep signals are used, each having a duration of 20 msec with 9 gaps of 33.3 msec each between each sweep signal. The numbers given above are examples and other combinations of number of sweep signals and gaps with respective time durations are possible. According to the disclosed technique, the total duration of an oral sample including at least one sweep signal and possibly zero or at least one gap between sweep signals should last between msec. It is noted as well that the time required for processor 112 to analyze reflected signal 144 is related to the number of sweep signals and gaps in an oral sample. Processor 112 may start to analyze an oral sample after the first sweep signal is received and in parallel to additional sweep signals being received in a single oral sample. Thus, the analysis of an oral sample can take anywhere from 10 msec to approximately 300 msec after an initial sweep signal has been received by processor 112.

In an embodiment, if the oral sample is authenticated, then processor 112 sends a signal to heater 140 to heat container 138 and thus provide delivered substance 146 to the user via delivery tube 136 and inhalation opening 130. Heater 140 may optionally be kept at a threshold temperature below which the substance in container 138 does not go through any chemical changes so as to shorten the amount of time needed to heat heater 140 to a sufficiently high temperature to deliver the substance to the user via inhalation opening 130. Thus, according to the disclosed technique, a low latency authentication system and method is achieved. In an embodiment, the inhalation system may be active as a default condition, and if an oral sample is not authenticated, an operation and/or function of the inhalation system may be deactivated or blocked.

In the case of age verification, there is no need for registration of a user with inhalation system 100. Instead, inhalation system 100 is trained using a classifier, a machine learning algorithm and the like, to identify the features of an oral signature of permitted users and optionally, the features of an oral signature of non-permitted users. Permitted users can include adolescents who are 14 years old and up and/or 16 years old and up. Permitted users can also include only adults aged 18 and up as well as only adults aged 21 and up or users aged 25 and up. Non-permitted users can include minors under the age of 14. Other age categorizations are possible. Since the human body tends to undergo physiological changes as the body ages, including changes in the size and number of teeth in the oral cavity as well as the shape and size of the oral cavity itself and oral tissue properties, with major changes typical to the transitions from childhood to adolescence and from adolescence to adulthood, the inventors have discovered that a large enough sample of oral signatures of individuals of different ages or age groups can be used to a train a classifier or a machine learning algorithm to identify features in an oral sample and thus classify the oral signature according to age or age groups. Once the training of inhalation system 100 is complete, the features of permitted and non-permitted users are stored in processor 112, memory 116 or in a cloud storage (not shown). The training of inhalation system 100 may be performed in a factory or laboratory setting and then embedded into processor 112 and/or memory 116. Optionally, this training may be updated by providing an upgrade from the factory during the lifetime of inhalation system 100. When a user wants to use inhalation system 100, an oral sample is taken, essentially as described above, and the features of the oral sample are compared to the stored features in inhalation system 100. Processor 112 can then authenticate the oral sample as belonging to an age class or group as per the stored features of each age class determined by the training. As described below in FIGS. 11 and 12, the authentication is based upon a probability of similarity between the features of the oral sample and the features stored during the training of inhalation system 100. Authenticating an oral sample by age according to the disclosed technique is thus a probability of a true positive (F-score) and can be defined as a percentage based on the number of oral samples taken to authenticate a user. In an embodiment the probability may be defined based on a number of recent authentication events. According to the disclosed technique, an oral sample taken over a single inhalation of inhalation system 100 may yield a probability of 90% true positives (F-score), whereas oral samples taken over three inhalations of inhalation system 100 may yield a probability of 95% true positives.

The probability of true positives (F-score) can increase as the features of an oral sample can be not only compared to a stored oral signature or stored oral features, but can also be correlated over time with previous oral samples to establish that the user is the same and also a permitted/registered user. For example, inhalation system 100 may enable delivery of the substance in container 138 over the course of a few inhalations (for example if inhalation system 100 is embodied as an e-cigarette) while sufficient oral samples are received to establish a robust authentication. If a probability of 95% true positives is not achieved by processor 112, then inhalation system 100 might cease to function or operate for a pre-determined amount of time (similar to how mobile phones lockdown any too many failed password attempts). As another example, inhalation system 100 may require a few initial inhalations of a user to establish a high enough probability (such as 95% true positives) for authentication before any delivery of the substance in container 138 is effected. Such an embodiment may be useful if the substance is a medicinal substance (for example medicinal cannabis). In an embodiment, a first inhalation is provided, and authentication is preformed, and substance delivery is permitted based on the oral sample collected in the first inhalation. In a later inhalation, authentication may be performed based on the oral sample collected in the later inhalation and/or on the collected oral samples of both the later and first inhalations. Similarly, each inhalation may be authenticated based on the oral sample collected in the same inhalation and/or on the collected oral samples of the same inhalation as well as one or more inhalations preceding it.

Inhalation system 100 in FIG. 1 is described and shown as including an acoustic wave generator as well as an acoustic wave sensor, meaning inhalation device generates the acoustic waves needed to register and then sample and authenticate an oral signature. However, in an embodiment of the disclosed technique, the inhalation system does not include an acoustic wave generator and includes only an acoustic wave sensor or a plurality of acoustic wave sensors. In such an embodiment, noise from the user and/or incoherent noise from the device or system are used as the source of acoustic waves which are detected by the acoustic wave sensor and from which features can be extracted and discerned to generate an oral signature of a user and/or the features of an oral signature of a permitted user. Incoherent noise from the device can be the sound of airflow through delivery tube 136 or any other structure of inhalation system 100. Incoherent noise can also be noise generated by components of inhalation system 100, such as the sound of heater 140 heating up the substance in container 138 or the sound produced when actuator 118 actuates. These sounds can be transmitted to the user's oral cavity as an acoustic signal which is reflected back towards the acoustic wave sensor. The main difference between an acoustic signal generated by acoustic wave generator 108 and the embodiment described herein is the control over and the predictability of the produced acoustic signals. There may be little if no control over incoherent noise which thus may also be unpredictable. Regardless, according to the disclosed technique, incoherent noise can be used as the acoustic signal for generating an oral signature and oral samples. The noise may be the ambient sound coming from the breathing of the user and/or any other detectable white noise coming from the user and/or the device or system of the disclosed technique. The noise may also include sound the user can make, such as grunts, coughs and/or the clearing of the throat. In such an embodiment, a plurality of acoustic wave sensors may be required to increase the sensitivity at which the acoustic signals coming from the user are detected so as to enable discernible features to be extracted from the received acoustic signals.

According to an embodiment of the disclosed technique, inhalation device 102 and/or replaceable component 104 may include a depth sensor (not shown) for detecting a depth to which a user has inserted replaceable component 104 into their mouth. For example, a portion of the device that is likely to come in contact with the lips or teeth may include one or more humidity sensors and/or pressure sensors (not shown). The sensors may be located along a path defined by the waveguides. When inserted in a user's mouth, the sensors may detect the location of the lips thereby allowing the estimation of the depth of replaceable component 104 in the user's mouth. The depth at which replaceable component 104 and in particular inhalation element 124 is inserted into the mouth of a user can influence the properties of acoustic signal 142 as well as reflected signal 144. The depth sensor can be used to alert the user that inhalation element 124 is not inserted deeply enough into their mouth, or vice-versa, inserted too far deep into their mouth, to get an accurate oral sample. In addition, the depth sensor can be used to correlate features of reflected signal 144 received from different depths of inhalation element 124 in the mouth of the user with features in a registered oral signature (or features of a permitted oral signature) taken from respective specific depths of inhalation element 124 in the mouth of the user.

It is noted that the description of FIG. 1 in general referred to an oral cavity and an oral signature, however inhalation system 100 can also be used nasally via a nasal signature. In an embodiment of the disclosed technique for nasal use, inhalation element 124 as an orifice element would be designed such that the distance between acoustic signal opening 126 and reflection signal opening 128 are substantially similar to the distance between the nostrils of a user and inhalation opening 130 may be positioned proximate to either one of, or both of, acoustic signal opening 126 and reflection signal opening 128 in order to inhale the substance in container 138 once their nasal signature has been authenticated. Inhalation system 100 can also be designed to be used with a single nostril, with inhalation element 124 having appropriate size, structure, and material so as to essentially seal the nostril when inhalation element 124 is properly inserted therein. In an embodiment, inhalation element 124 may be designed such that acoustic signal opening 126 and reflection signal opening 128 fit into one nostril and inhalation opening fits into the second nostril. Other arrangements are possible and can be designed appropriately by the worker skilled in the art.

The disclosed technique as described in FIG. 1 has been described regarding an inhalation system in which a user either inhales a delivered aerosol at ambient temperature of a substance or inhales a delivered aerosol or vapor of a heated substance. However, the disclosed technique is not limited to such systems and devices and can be embodied in other oral devices which do not require inhalation, such as a thermometer, or otherwise may be configured as a dedicated authentication probe or dongle. In an embodiment the disclosed technique may be applied in electronic systems and devices which are inserted into other human cavities, such as the nasal, oral, or tympanic cavities, but do not necessarily require inhalation, otherwise known as non-inhalation systems and devices. Non-inhalation systems and devices as embodied with the disclosed technique can be broken down into two further categories, exhalation systems and devices and systems and devices which do not require inhalation or exhalation.

Exhalation systems and devices can include medical exhalation devices, nebulizers, respirators with an exhalation valve as well as breathalyzers and even electronic musical wind instruments. In an embodiment, the system of the disclosed technique may not include a device and a replaceable component, as shown in FIG. 1, but may include a device which incorporates some parts of the replaceable component as described above, including an acoustic wave generator, an acoustic wave sensor, a processor, a power supply, output and input acoustic waveguides and an acoustic signal opening and a reflection signal opening. Such a device might also include a memory or access to a memory storing an oral signature and/or features of the oral signature of an age group of users (either permitted or non-permitted). Thus such an embodiment will not include a delivery tube, a container nor a heater however would include a hollow or tube of sorts for blowing and exhaling into the system and possibly a component (e.g., a chamber or a sensor) to collect a sample of exhaled air. Such a component could be a sample collector for collecting a sample of exhaled air for analysis by the device. Such an embodiment of the disclosed technique would work substantially as inhalation system 100 functions to register and then authenticate a user based on an oral signature of the user's cavity, however instead of the authentication providing an indication which then allows a substance to be delivered to the user or not, the authentication may provide an indication which either allows or prevents at least one function of the exhalation system or a device or apparatus which is either paired or coupled with the exhalation system. For example, in the case of an electronic wind musical instrument, the registration and then authentication of a user based on their oral signature may enable functions on the musical instrument to either work or not. For example, if a user is not authenticated, then the musical instrument may turn off for a pre-determined amount of time or only have limited functionality. In the case of a breathalyzer, the breathalyzer may be associated with controlling the operation of a vehicle, for example by being paired with a key fob of a vehicle which the user is authorized to use, subject to proving sobriety. A registered user may be required to authenticate their oral signature with the breathalyzer which can be used to enable or disable the key fob upon confirmation of sobriety and thus prevent a person from entering and driving the car if intoxicated and/or not a registered user. For example, if the user attends a bar and becomes inebriated, the user will have to authentic their oral signature with the breathalyzer, which will also determine the amount of alcohol in the user's blood, which can then enable or disable the key fob of the user's car. The user thus will not be able to give the breathalyzer to a friend who is not inebriated to enable the key fob as the indication to enable or disable the key fob is paired with the breathalyzer's authentication of the measurement of the amount of alcohol in a user's blood with the registered user.

Devices which do not require any inhalation or exhalation but are nonetheless used with an oral cavity of a human can include thermometers inserted into the oral cavity as well as thermometers inserted into the tympanic cavity. Such systems and devices do not require a user to inhale or exhale to function but simply work by placing the system or device in a human cavity. In embodiments like these, the system of the disclosed technique may not include a device and a replaceable component, as shown in FIG. 1, but may only include a device (having a single device body), including at minimum an acoustic wave generator, an acoustic wave sensor, a processor, a power supply, output and input acoustic waveguides and an acoustic signal opening and a reflection signal opening. Thus, such an embodiment may not include a delivery tube, a container nor a heater however it may include a rod, a member or a tip which is inserted into the cavity. The rod, member or tip may be a thermocouple (such as in the case of an oral thermometer) or a hollow for transmitting and receiving infrared radiation (such as in the case of a tympanic thermometer). Such an embodiment of the disclosed technique would work substantially as inhalation system 100 functions to register and then authenticate a user based on a cavity signature of the user's cavity, however instead of the authentication providing an indication which then allows a substance to be delivered to the user or not, the authentication may provide information from the system or device to a memory or server (not shown). For example, in the case of a thermometer used in a hospital setting, the measured temperature (either orally or aurally) of a user can be stored in a memory or server linked to a patient record of the user. The authentication of the non-inhalation/exhalation system or device thus identifies the user and can then link any measurement made by the non-inhalation/exhalation system or device to a digital record of the user.

Figure 2C:
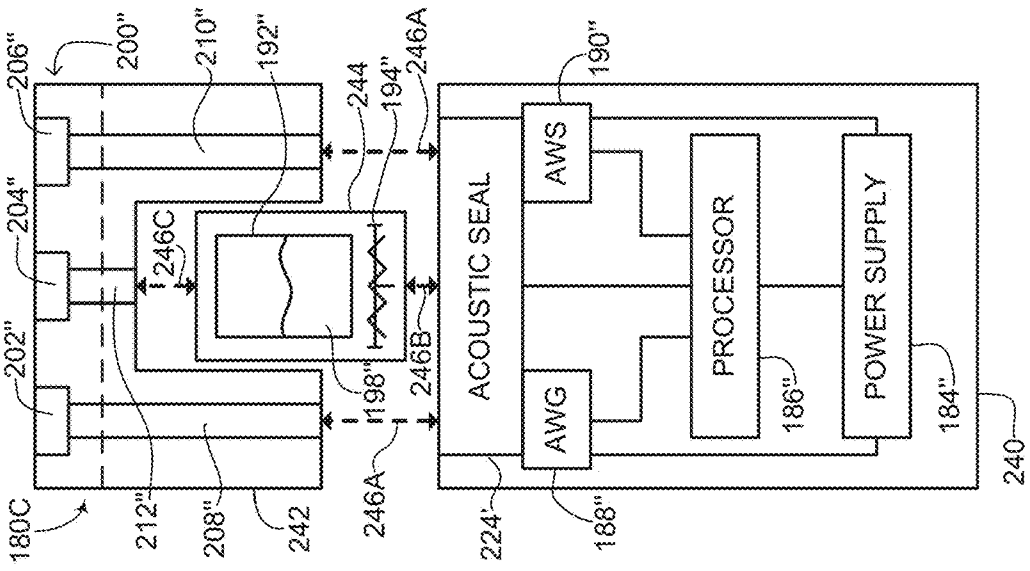
FIGS. 2A-2C are schematic illustrations of various configurations of the inhalation system of FIG. 1, constructed and operative in accordance with an embodiment of the disclosed technique.
Figure 2B:
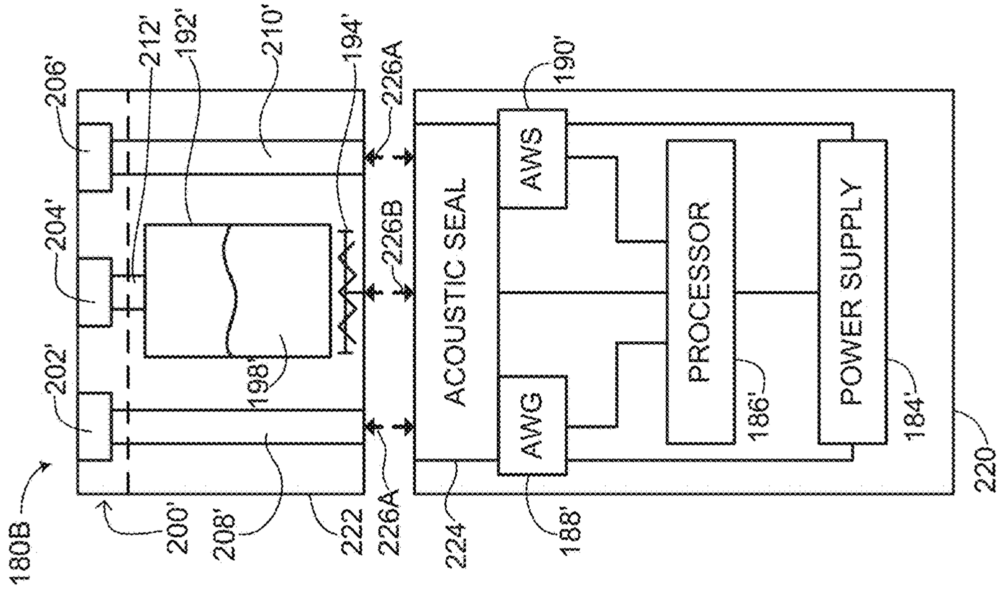
Figure 2A:
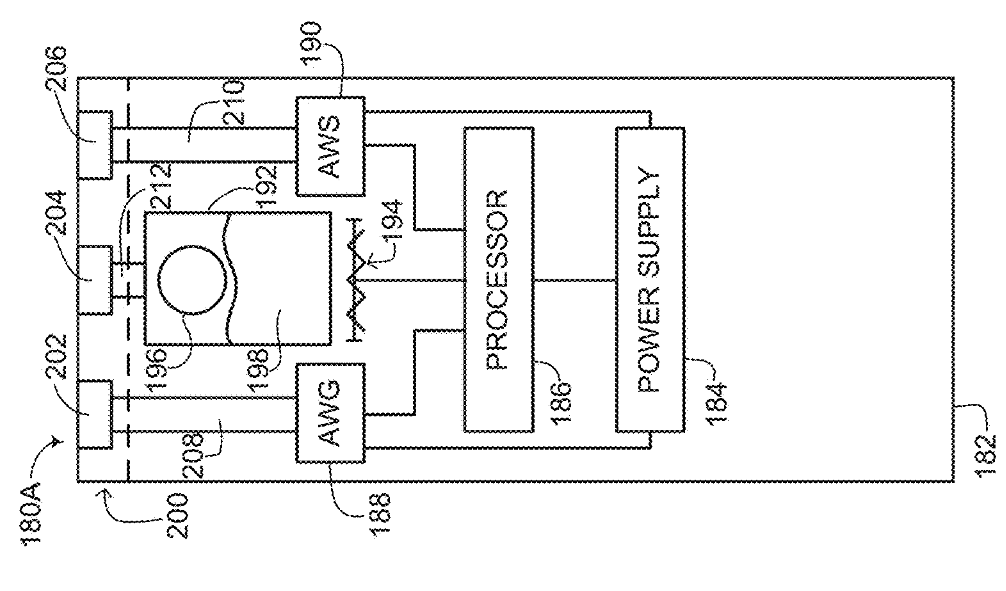

Reference is now made to FIGS. 2A-2C, which are schematic illustrations of various configurations of the inhalation system of FIG. 1, generally referenced 180A, 180B and 180C, constructed and operative in accordance with an embodiment of the disclosed technique. The disclosed technique can be embodied in various configurations and is not limited to the configuration shown above in FIG. 1. Reference is now made to FIG. 2A, which shows a single component embodiment of the disclosed technique. Inhalation system 180A includes a single device body 182 which includes a power supply 184, a processor 186, an acoustic wave generator (herein abbreviated AWG) 188, an acoustic wave sensor (herein abbreviated AWS) 190, a container 192, a heater 194, an inhalation element 200 which includes an acoustic signal opening 202, an inhalation opening 204 and a reflection signal opening 206, an output acoustic waveguide 208, an input acoustic waveguide 210 and a delivery hollow (or tube) 212. Power supply 184 is coupled with processor 186, AWG 188, AWS 190, and heater 194. Processor 186 is coupled with AWG 188, AWS 190 and heater 194. AWG 188 is coupled with acoustic signal opening 202 via output acoustic waveguide 208, AWS 190 is coupled with reflection signal opening 206 via input acoustic waveguide 210 and container 192 is coupled with inhalation opening 204 via delivery hollow 212. Inhalation system 180A works substantially similar to inhalation system 100 (FIG. 1) except that all components and elements are contained within single device body 182. The system of FIG. 2A may include additional components (such as an actuator, a memory, a user interface and the like, as described above in FIG. 1) which are not shown in order to simplify the figure. Output acoustic waveguide 208 and input acoustic waveguide 210 are acoustically sealed respectively with AWG 188 and AWS 190. Container 192 may include an opening 196 through which container 192 can be filled, refilled or emptied. Container 192 is shown containing a substance 198, which may be a liquid or a solid. Once substance 198 is used up by a user, opening 196 can be opened and container 192 can be refilled with the same, or different, substance. Optionally container 192 cannot be refilled, and once emptied, inhalation system 180A may be discarded. As compared with inhalation system 100, inhalation system 180A may have no replaceable components.

Reference is now made to FIG. 2B, which shows a two component embodiment of the disclosed technique, similar to the embodiment shown in FIG. 1. Inhalation system 180B includes an inhalation device body 220 and a replaceable component 222. Inhalation device body 220 includes a power supply 184', a processor 186', an AWG 188', an AWS 190' and an acoustic seal 224. Replaceable component 222 includes a container 192', a heater 194', an inhalation element 200' which includes an acoustic signal opening 202', an inhalation opening 204' and a reflection signal opening 206', an output acoustic waveguide 208', an input acoustic waveguide 210' and a delivery hollow (or tube) 212'. Replaceable component 222 is designed to be attached and detached, or inserted and removed from inhalation device body 220, as was described above in FIG. 1.

Power supply 184' is coupled with processor 186', AWG 188' and AWS 190'. When replaceable component 222 is attached to inhalation device body 220, power supply 184' is also coupled with heater 194', as shown by an arrow 226B. Processor 186' is coupled with AWG 188' and AWS 190' and can optionally be coupled with heater 194' when replaceable component 222 is attached to inhalation device body 220. AWG 188' and AWS 190' are coupled with acoustic seal 224. When replaceable component 222 is inserted and coupled with inhalation device body 220, output acoustic waveguide 208' is coupled with AWG 188' via acoustic seal 224 and input acoustic waveguide 210' is coupled with AWS 190' also via acoustic seal 224, as shown by plurality of arrows 226A. Container 192' is coupled with inhalation opening 204' via delivery hollow 212'. Container 192' contains a substance 198'. Inhalation system 180B works substantially similar to inhalation system 100 (FIG. 1) and may have a two-part design, with inhalation device body 220 being more permanent and replaceable component 222 being disposable. The system of FIG. 2B may include additional components (such as an actuator, a memory, a user interface and the like, as described above in FIG. 1) which are not shown in order to simplify the figure.

Acoustic seal 224 acoustically seals AWG 188' and 190' with their respective waveguides such that generally no sound enters or exits either waveguide through their region of contact when replaceable component 222 is coupled with inhalation device body 220. Optionally, no air enters or exits either waveguide through their region of contact when replaceable component 222 is coupled with inhalation device body 220. The configuration of components and elements in inhalation system 180B is an example, and other variations of the two-part design are possible. For example, in an embodiment, acoustic seal 224 may be part of replaceable component 222 and not part of inhalation device body 220. In an embodiment, acoustic seal 224 may comprise a plurality of acoustic seals, for example a respective acoustic seal positioned and dedicated to each waveguide. In an embodiment, AWG 188' and AWS 190' may not be in inhalation device body 220 and may be in replaceable component 222. In such an embodiment, AWG' 188 and AWS 190' are acoustically sealed with their respective waveguides and might not require a separate acoustic seal as shown in FIG. 2B. Optionally, heater 194' may be positioned in inhalation device body 220 as a permanent element. In an embodiment, container 192' may be refillable such as container 192 (FIG. 2A), including an opening (not shown) for refilling the container. Such an embodiment may be used when AWG 188' and AWS 190' are part of replaceable component 222.

Reference is now made to FIG. 2C, which shows a three component embodiment of the disclosed technique, similar to yet different than the embodiment shown in FIG. 2B. Inhalation system 180C includes an inhalation device body 240, an inhalation device headpiece 242 and a replaceable component 244. Inhalation device body 240 includes a power supply 184", a processor 186", an AWG 188", an AWS 190" and an acoustic seal 224'. Inhalation device headpiece 242 includes an inhalation element 200" which includes an acoustic signal opening 202", an inhalation opening 204" and a reflection signal opening 206", an output acoustic waveguide 208", an input acoustic waveguide 210" and a delivery hollow (or tube) 212". Replaceable component 244 includes a container 192" and a heater 194". Inhalation device body 240 and inhalation device headpiece 242 are permanent components designed to be coupled and attached and also decoupled and detached. Inhalation device headpiece 242 is designed with an opening in which replaceable component 244 can be attached and detached, or inserted and removed from inhalation device body 240 and inhalation device headpiece 242.

Power supply 184" is coupled with processor 186", AWG 188" and AWS 190". When replaceable component 244 is attached to inhalation device body 240, power supply 184" is also coupled with heater 194", as shown by an arrow 246B. Processor 186" is coupled with AWG 188" and AWS 190" and can optionally be coupled with heater 194" when replaceable component 244 is attached to inhalation device body 240. AWG 188" and AWS 190" are coupled with acoustic seal 224'. When inhalation device headpiece 242 is inserted and coupled with inhalation device body 240, output acoustic waveguide 208" is coupled with AWG 188" via acoustic seal 224' and input acoustic waveguide 210" is coupled with AWS 190" also via acoustic seal 224', as shown by plurality of arrows 246A. When inhalation device headpiece 242 is inserted and coupled with inhalation device body 240, container 192" is coupled with inhalation opening 204" via delivery hollow 212" as shown by an arrow 246C, and as mentioned above, heater 194" may be coupled with power supply 184". Container 192" contains a substance 198". Inhalation system 180C works substantially similar to inhalation system 100 (FIG. 1) and has a three-part design, with inhalation device body 240 and inhalation device headpiece being more permanent and replaceable component 244 being disposable. The system of FIG. 2C may include additional components (such as an actuator, a memory, a user interface and the like, as described above in FIG. 1) which are not shown in order to simplify the figure.

Acoustic seal 224' acoustically seals AWG 188" and 190" with their respective waveguides such that generally no sound enters or exits either waveguide through their region of contact when inhalation device headpiece 242 is coupled with inhalation device body 240. Optionally, no air enters or exits either waveguide through its respective region of contact. The configuration of components and elements in inhalation system 180C is an example, and other variations of the three-part design are possible. For example, in an embodiment, acoustic seal 224' may be part of replaceable component 244, inhalation device headpiece 242 or both and not part of inhalation device body 240. In an embodiment, AWG 188" and AWS 190" may not be in inhalation device body 220 and may be in inhalation device headpiece 242. In such an embodiment, AWG" 188 and AWS 190" are acoustically sealed with their respective waveguides and might not require a separate acoustic seal as shown in FIG. 2C. In an embodiment, heater 194" may be positioned in inhalation device body 240 as a permanent element. In an embodiment, container 192" may be refillable such as container 192 (FIG. 2A), including an opening (not shown) for refilling the container.

General reference is now made to FIGS. 3A-10, which represent example embodiments of the disclosed technique, designed with real world constraints using computer-aided design software. In FIGS. 3A-10, various perspectives of an example embodiment of the disclosed technique are shown from various views (orthogonal, perspective, cross-section and exploded). Components are thus labeled using identical reference numbers. The examples of FIGS. 3A-10 are merely brought to show further examples of the disclosed technique and are not meant to be limiting the disclosed technique in any way. Other designs, configurations and arrangements of the components of the disclosed technique as described above schematically in FIGS. 1 and 2A-2C may be applicable as well.

Figure 3A:
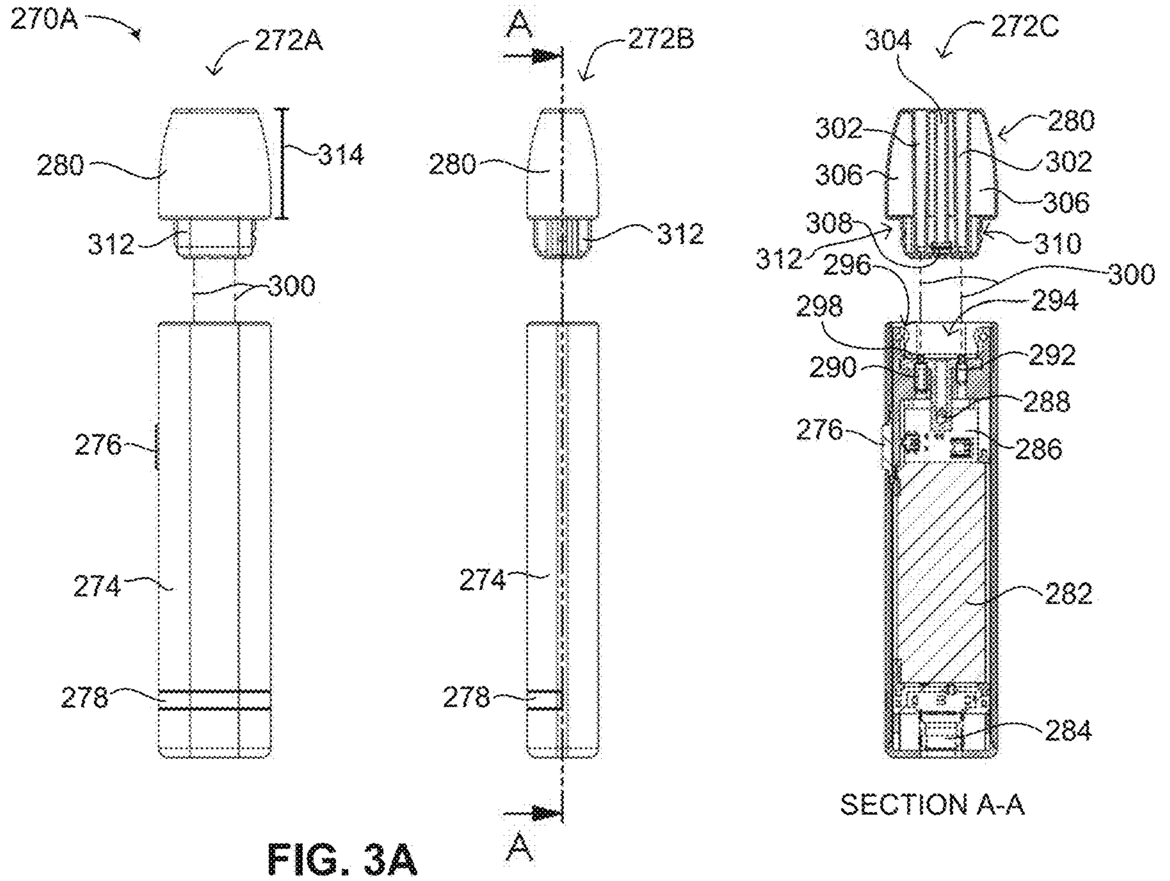
FIGS. 3A-3B are orthogonal and cross-section illustrations of a first example inhalation system, constructed and operative in accordance with some embodiments of the disclosed technique.
Figure 3B:
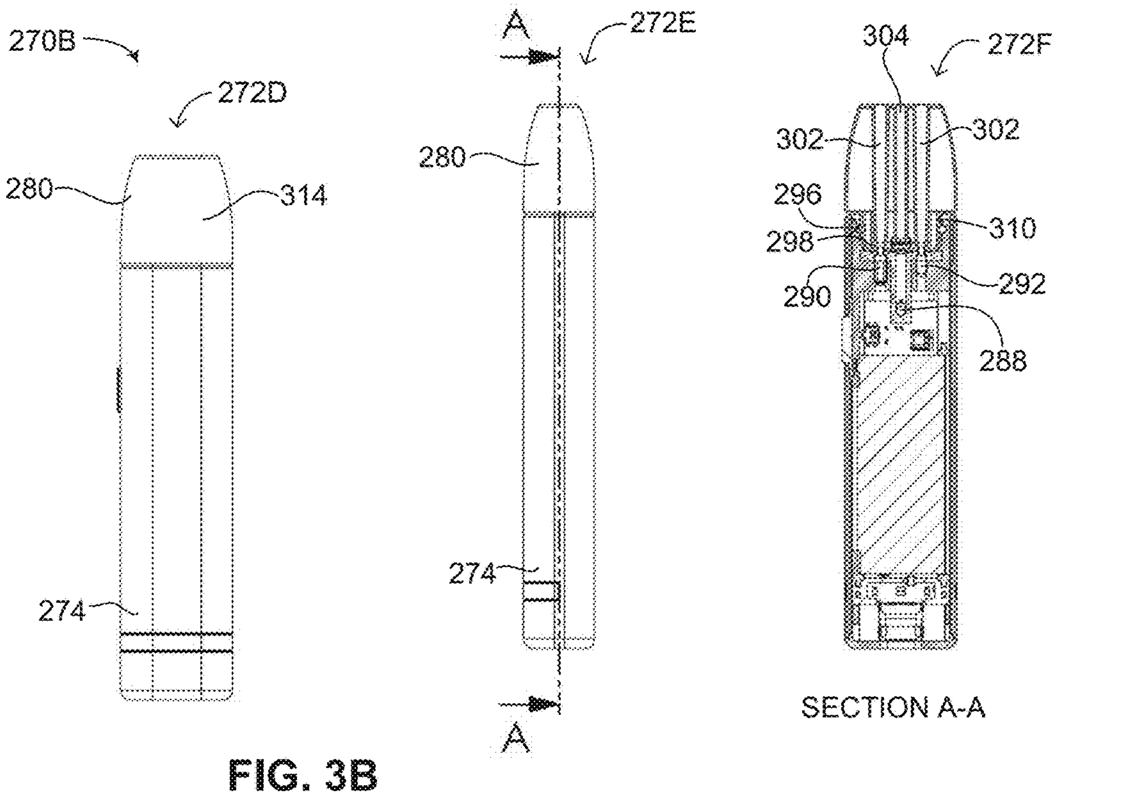

Reference is now made to FIGS. 3A-3B, which are orthogonal and cross-section illustrations of a first example inhalation system, generally referenced 270A and 270B, constructed and operative in accordance with some embodiments of the disclosed technique. First example inhalation system 270A is shown in three different views, a frontal orthogonal view 272A, a side orthogonal view 272B with cross-section mark A-A and a cross-section view 272C along cross-section mark A-A. Frontal orthogonal view 272A shows a device body 274 and a pod 280, containing a substance (not shown), in a detached position. Pod 280 is substantially similar to replaceable component 104 (FIG. 1). As shown, pod 280 includes a mouthpiece 314 and a connector 312. Mouthpiece 314, or a portion of mouthpiece 314, is inserted into the user's oral cavity when first example inhalation system 270A is to be used. As shown in FIG. 3A, device body 274 and pod 280 are shown as separate components. Plurality of lines 300 shows how connector 312 couples and inserts into device body 274. Device body 274 may include an actuator 276 as well as an indicator 278. Actuator 276 is shown as a switch or button in FIG. 3A. Indicator 278 may be a light indicator which can indicate various signals to the user (such as by a flashing pattern, by changing color and the like).

Cross-section view 272C shows the inner components of first example inhalation system 270A not visible in orthogonal views 272A and 272B. As shown, device body 274 includes a battery 282, substantially similar to power supply 114 (FIG. 1), which may be rechargeable. A charging port 284 enables battery 282 to be coupled with a power source for recharging, for example. Device body 274 also includes a printed circuit board (herein abbreviated PCB) 286, which is coupled electrically with actuator 276. PCB 286 may include various electronic circuits and arrays forming a processor for controlling the elements of first example inhalation system 270A, including an acoustical codec unit (not shown). PCB 286 may include a memory (not shown). Shown as well are an AWG 290 (for example a speaker) and an AWS 292 (for example a microphone). The aforementioned acoustic codec unit is used to control AWG 290 and AWS 292. Positioned between AWG 290 and AWS 292 is a pressure sensor 288. As shown, pod 280 includes two waveguides 302, an airway 304 (substantially similar to delivery tube 136), a container 306 and a heating element 308. Container 306 may contain a substance as a liquid which can be heated via heating element 308 and then inhaled as a vapor and/or an aerosol. Heating element 308 is positioned directly over the entrance of airway 304 and as shown, container 306 occupies a significant volume of mouthpiece 314. Connector 312 is designed to fit into a hollow 294 of device body 274. Connector 312 may include at least one indentation 310 to which a respective at least one matching protrusion 296 in hollow 294 may couple with to secure connector 312 in hollow 294.

Pressure sensor 288 can act as a trigger indicating that a user is inhaling via airway 304 due to a change in airflow in airway 304 as detected by pressure sensor 288. A distal end of hollow 294 includes an acoustic seal 298, covering the ends of AWG 290 and AWS 292. As shown, pod 280 is designed such that waveguides 302 insert respectively into AWG 290 and AWS 292 via acoustic seal 298 when connector 312 is positioned inside hollow 294. Heating element 308 is electrically coupled with PCB 286 when connector 312 is positioned inside hollow 294. As clearly seen in FIG. 3B, pressure sensor 388 is aligned with airway 304 which is the same airway through which a user would inhale a substance contained in container 306.

First example inhalation system 270B is shown in three different views, a frontal orthogonal view 272D, a side orthogonal view 272E with cross-section mark A-A and a cross-section view 272F along cross-section mark A-A. Frontal orthogonal view 272B shows device body 274 and pod 280 in an attached position. When attached, mouthpiece 314 of pod 280 is visible. As specifically shown in cross-section view 272F with the connector inserted into the hollow of the device body, at least one indentation 310 matches up with at least one protrusion 296 to keep pod 280 firmly attached to device body 274 when first example inhalation system 270B is in use. Also clearly shown are waveguides 302 coupled respectively into AWG 290 and AWS 292 via acoustic seal 298. Shown as well is the heating element positioned over pressure sensor 288 which lines up directly with airway 304.

Figure 4A:
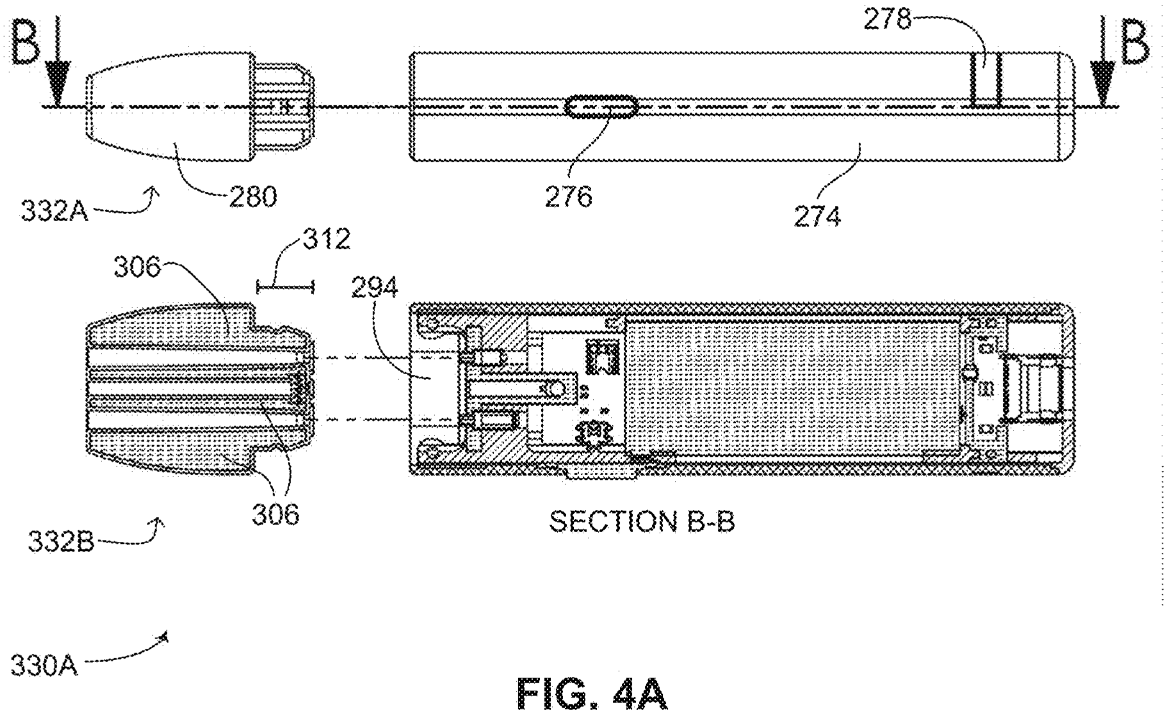
FIGS. 4A-4B are additional orthogonal and cross-section illustrations of the first example inhalation system of FIGS. 3A-3B, constructed and operative in accordance with an embodiment of the disclosed technique.
Figure 4B:
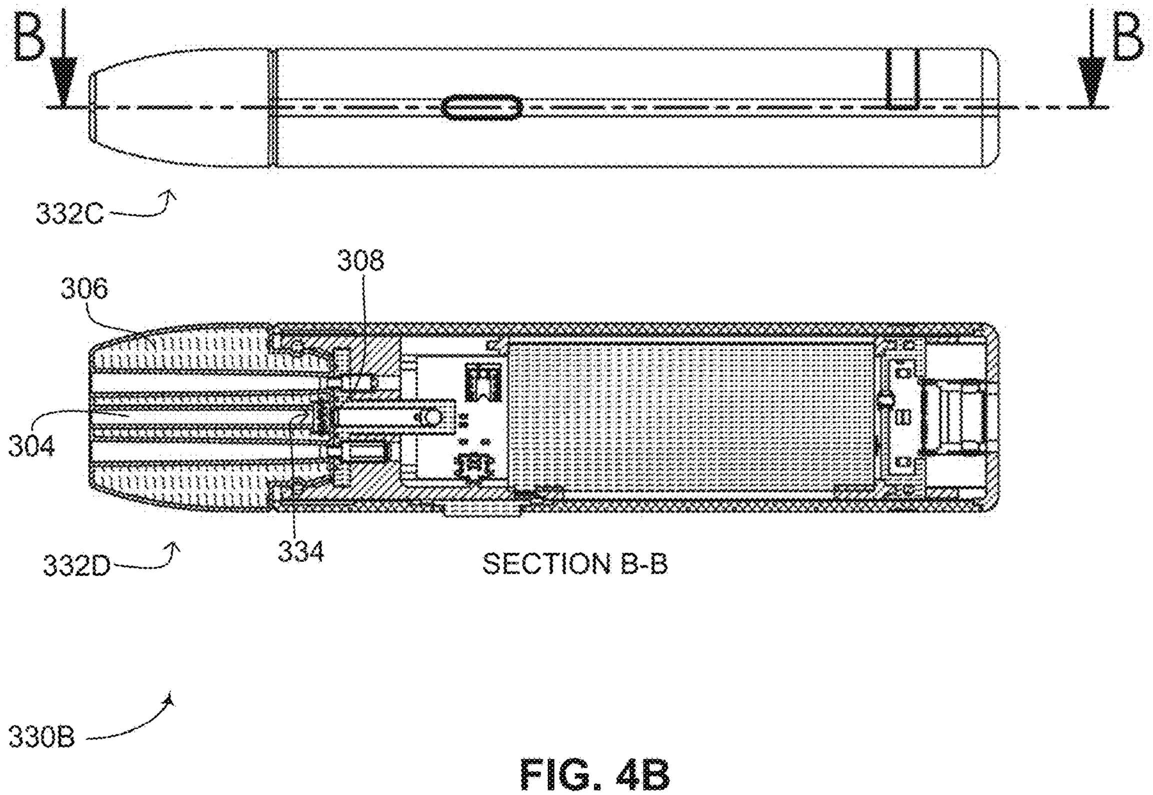

Reference is now made to FIGS. 4A-4B, which are additional orthogonal and cross-section illustrations of the first example inhalation system of FIGS. 3A-3B, generally referenced 330A and 330B, constructed and operative in accordance with an embodiment of the disclosed technique. First example inhalation system 330A is shown in two different views, a side orthogonal view 332A with cross-section mark B-B and a cross-section view 332B along cross-section mark B-B. Side orthogonal view 332A shows device body 274 and pod 280 in a detached position. As seen, actuator 276 may be small as compared to the size of device body 274. In addition, indicator 278 may be positioned on one side of device body 274. Cross-section view 332B shows connector 312 which fits into hollow 294. As seen, container 306 can be designed to maximize its volume and thus the volume of substance (for example as a liquid) that can be contained in pod 280. As shown, container 306 extends into connector 312. First example inhalation system 330B is shown in two different views, a side orthogonal view 332C with cross-section mark B-B and a cross-section view 332D along cross-section mark B-B. Side orthogonal view 332B shows the device body and the pod in an attached position. Shown is how container 306 is contained in part of the hollow in the device body. Shown as well is how a distal end 334 of airway 304 is positioned directly over heating element 308 when the device body and the pod are in an attached position.

Figure 5:
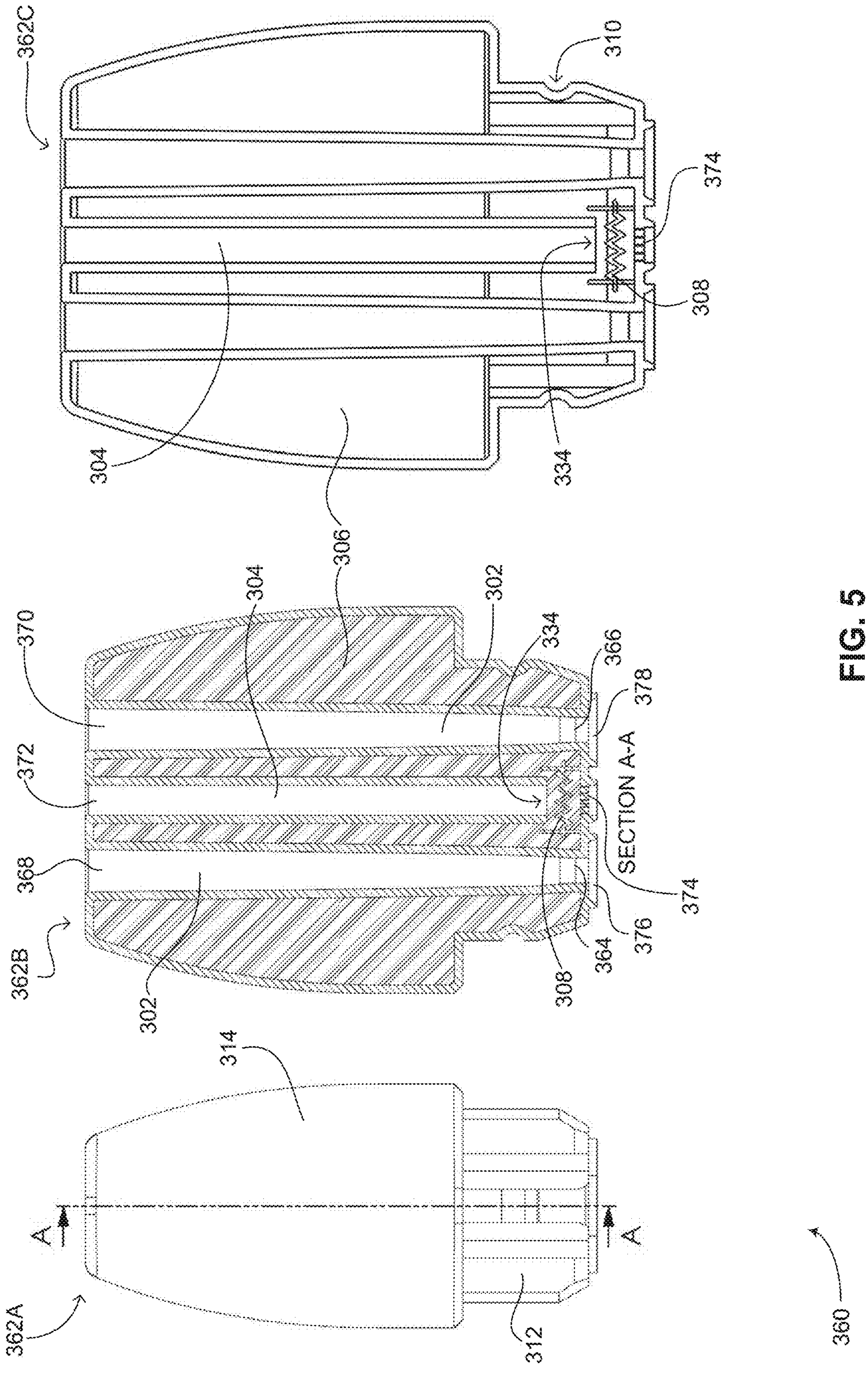
FIG. 5 is an orthogonal and cross-section illustration of the replaceable component of the first example inhalation system of FIGS. 3A-3B, constructed and operative in accordance with an embodiment of the disclosed technique.

Reference is now made to FIG. 5, which is an orthogonal and cross-section illustration of the replaceable component of the first example inhalation system of FIGS. 3A-3B, generally referenced 360, constructed and operative in accordance with an embodiment of the disclosed technique. Replaceable component 360 (substantially equivalent to pod 280 (FIG. 3A)) is shown in three different views, a side orthogonal view 362A with cross-section mark A-A, a first cross-section view 362B along cross-section mark A-A as well as a second cross-section view 362C along a similar cross-section. First cross-section view 362B shows that waveguides 302 include proximal ends 368 and 370 as well as distal ends 364 and 366. As can be seen, proximal ends 368 and 370 taper towards distal ends 364 and 366, thus giving waveguides 302 a changing diameter along its length. Proximal ends 368 and 370 may include respective membranes (not shown), covering the openings into waveguides 302 and thus preventing dirt, debris and dust from entering. Distal ends 364 and 366 respectively include acoustic sealant surfaces 376 and 378 which couple waveguides 302 to the AWG and AWS (not shown in FIG. 5) via the acoustic seal. Airway 304 is shown with an outlet 372 through which a user can inhale. Clearly shown is heating element 308 positioned directly in line with distal end 334 of airway 304. Shown as well is that container 306 occupies most of the volume of replaceable component 360 and that distal end 334 is open to container 306. When heating element 308 heats container 306, the substance in container 306 can enter airway 304 as a vapor through distal end 334 and travel towards outlet 372 towards a user's oral cavity. The vapor may cool or condense to some extent and thus become an aerosol before it is inhaled by the user. Shown as well is an inlet 374 through which air can enter airway 304 when a user inhales. Lines (not referenced) directly above inlet 374 show the electrical connection heating element 308 makes with the device body when replaceable component 360 is inserted into the device body. As shown, waveguides 302 as well as airway 304 may not be added components to replaceable component 360 but may merely be hollow spaces formed within replaceable component 360. Second cross-section view 362C shows the positioning of heating element 308 directly in line with distal end 334 as well as inlet 374 and the aforementioned electrical connection of heating element 308 to the PCB when the replaceable component is inserted into the device body.

Figure 6A:
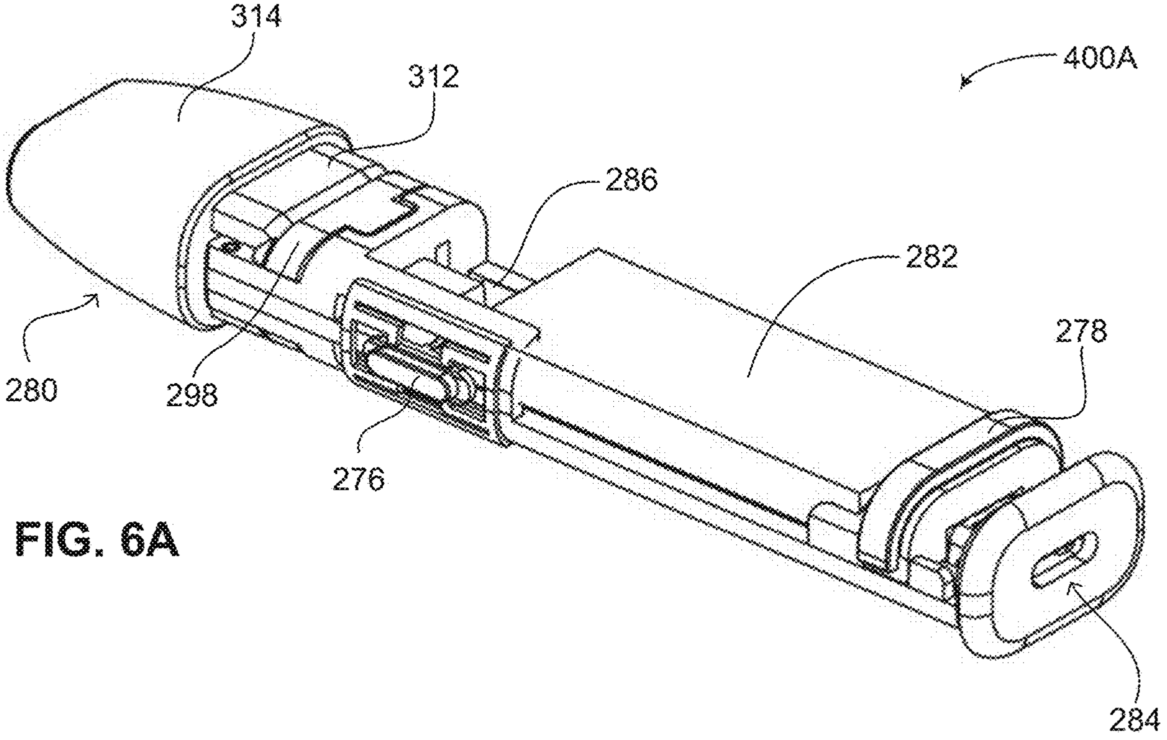
FIGS. 6A-6B are perspective illustrations of the first example inhalation system of FIGS. 3A-3B, constructed and operative in accordance with an embodiment of the disclosed technique.
Figure 6B:
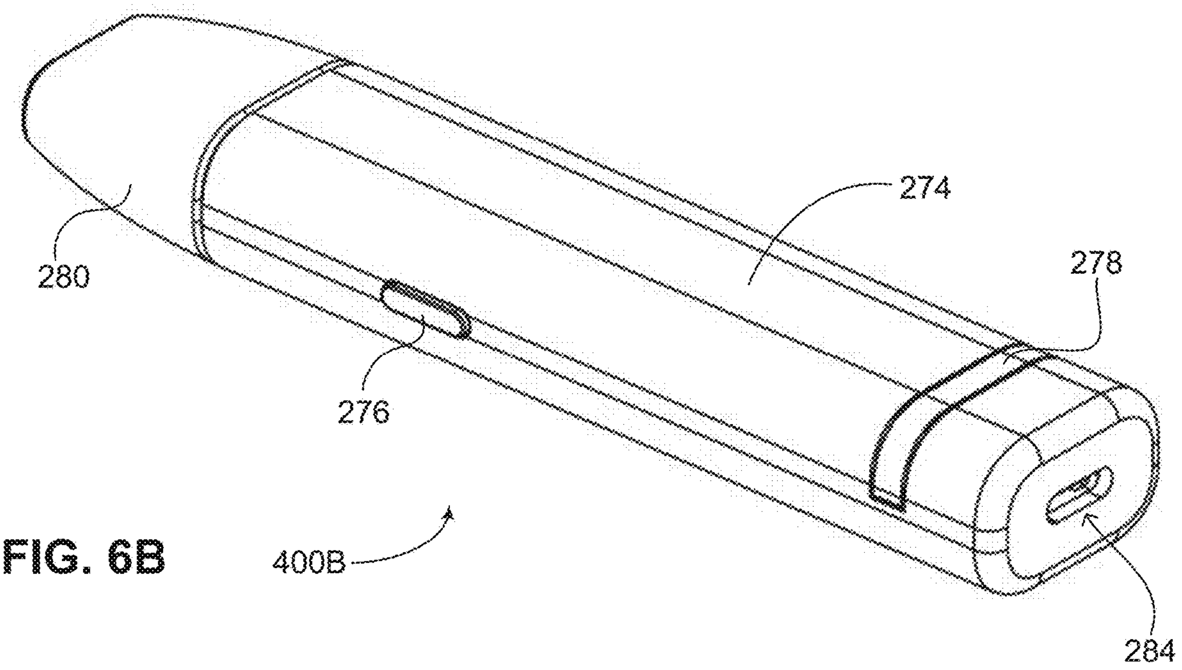

Reference is now made to FIGS. 6A-6B, which are perspective illustrations of the first example inhalation system of FIGS. 3A-3B, generally referenced 400A and 400B, constructed and operative in accordance with an embodiment of the disclosed technique. With reference to FIG. 6A, first example inhalation system 400A is shown in a perspective see-through view, showing a sense of volume of the components of first example inhalation system 400A. As can be seen battery 282 occupies a significant volume of the device body. Connector 312 is shown when inserted in the device body to be flush again acoustic seal 298. With reference to FIG. 6B, first example inhalation system 400B is shown in a perspective view showing the general outside design of first example inhalation system 400B. Device body 274 is designed to be handheld, with actuator 276 positioned where a user's thumb would be when holding first example inhalation system 400B in the palm of the hand.

Figure 7A:
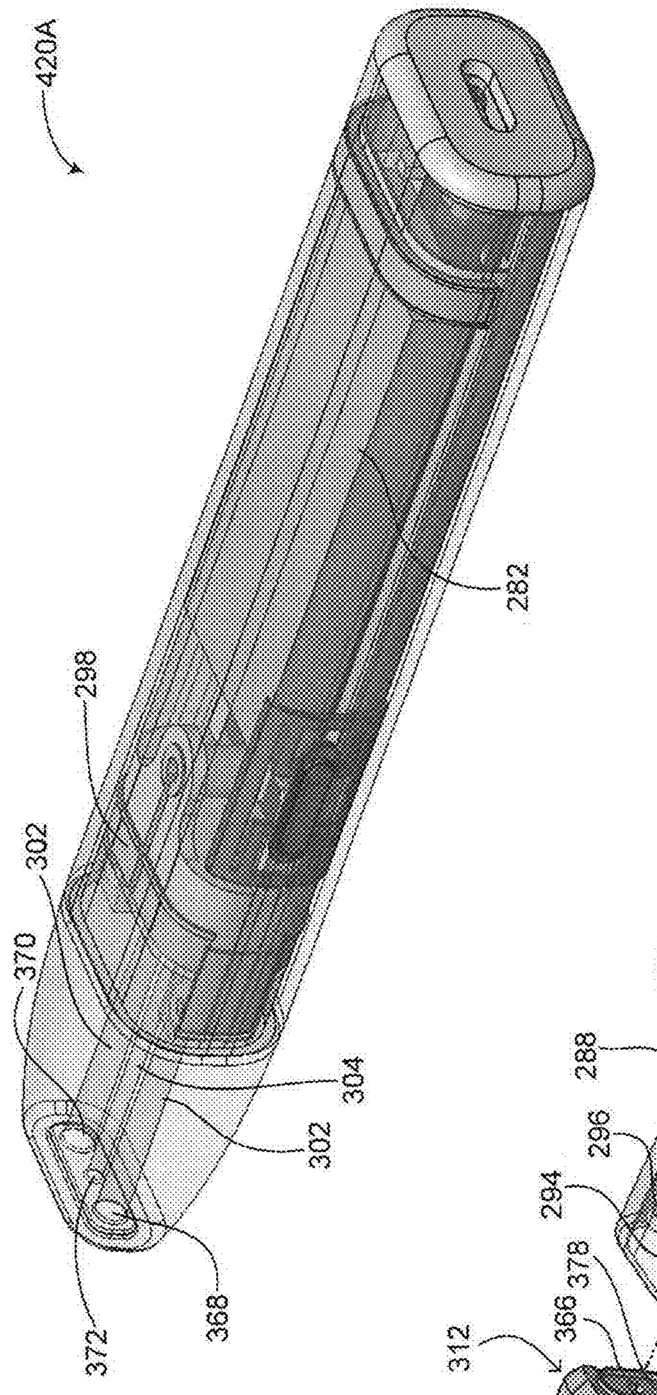
FIGS. 7A-7D are additional perspective illustrations of the first example inhalation system of FIGS. 3A-3B, constructed and operative in accordance with an embodiment of the disclosed technique.
Figure 7B:
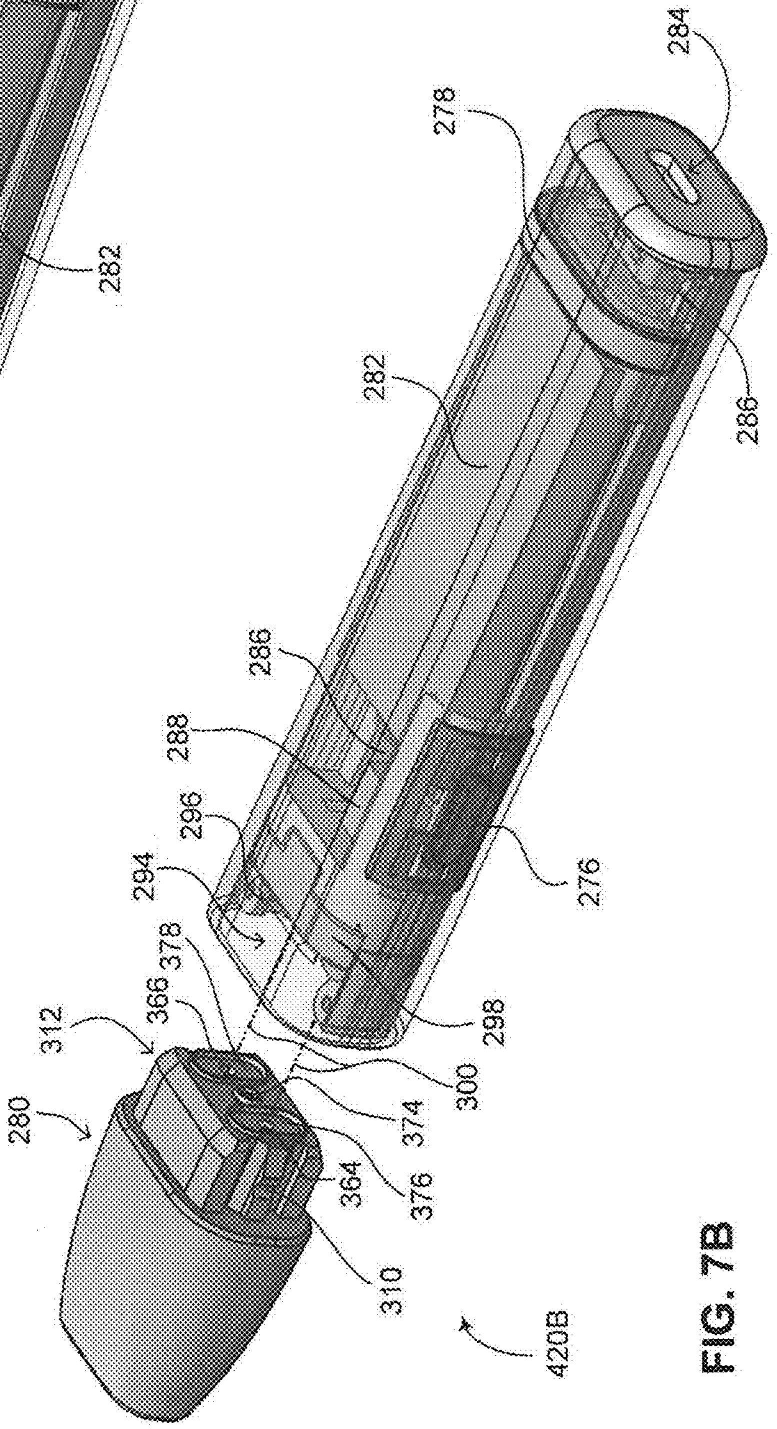

Reference is now made to FIGS. 7A-7D, which are additional perspective illustrations of the first example inhalation system of FIGS. 3A-3B, generally referenced 420A-420D, constructed and operative in accordance with an embodiment of the disclosed technique. With reference to FIG. 7A, first example inhalation system 420A is shown in a see-through perspective view showing the top and one side of the system. As can be seen the mouthpiece shows waveguides 302 and airway 304 extending from proximal ends 368 and 370 (which are substantially openings) into acoustic seal 298. Outlet 372, through which a user can inhale, leads to airway 304 which extends along the length of the mouthpiece, substantially parallel to waveguides 302. With reference to FIG. 7B, first example inhalation system 420A is shown in a see-through perspective view showing the top and one side of the system in which pod 280 is detached from the device body. Clearly shown are the 3D shapes of at least one indentation 310 in connector 312 and at least one protrusion 296 in hollow 294. Also clearly shown are plurality of lines 300 which show how pod 280 inserts into the device body. Shown as well are distal ends 364 and 366 which are substantially openings into the waveguides (not visible) and acoustic sealant surfaces 376 and 378 which surround distal ends 364 and 366 and to which acoustic seal 298 couples with when pod 280 is inserted into the device body. Inlet 374 is also visible between distal ends 364 and 366. It can also be seen that PCB 286 may extend the length of the device body under battery 282.

Figure 7C:
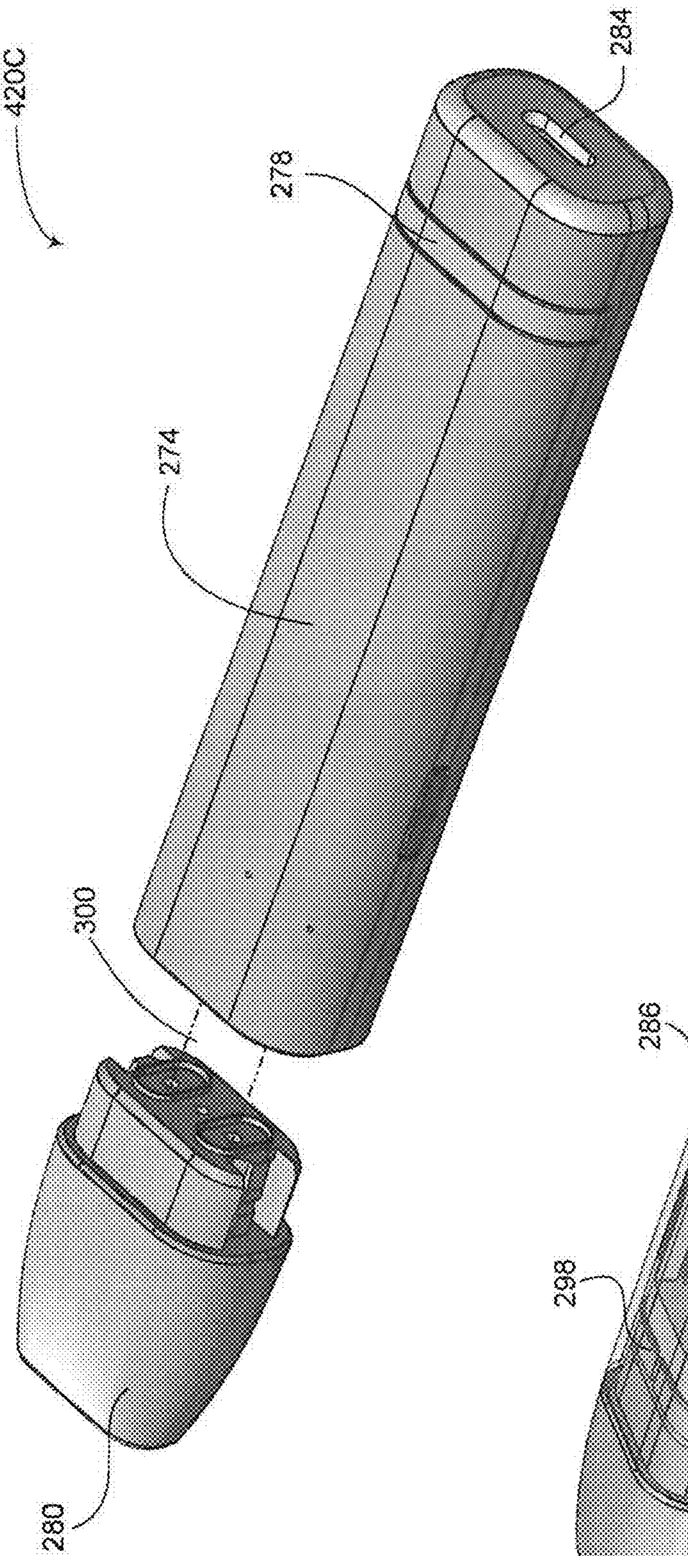
Figure 7D:
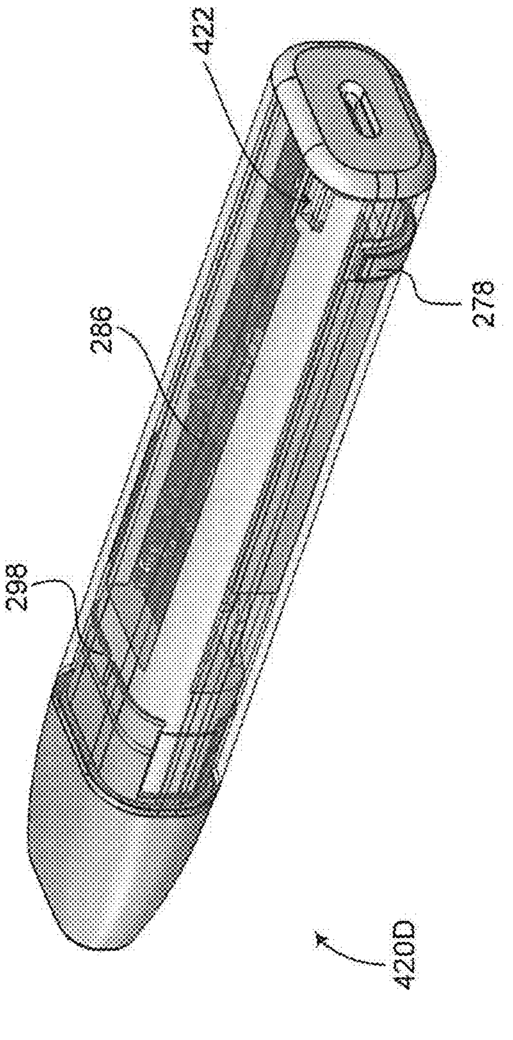

With reference to FIG. 7C, first example inhalation system 420C is shown in a perspective view showing the top and one side of the system in which pod 280 is detached from device body 274. Indicator 278 is shown as well as charging port 284 along with plurality of lines 300 which show how pod 280 inserts into device body 274. First example inhalation system 420C is shown having a sleek design with bevels and curves. Other designs are possible, and examples are given below in FIG. 10. With reference to FIG. 7D, first example inhalation system 420D is shown in a see-through perspective view showing the back and another side of the system in which the pod is inserted into the device body. As clearly seen, PCB 286 extends along the length of the device body and allows for sufficient electronic components and circuits to house a processor capable of performing the functions described above regarding processor 112 (FIG. 1). Shown as well is a wireless transceiver 422 housed in the back side of the device body. Wireless transceiver 422 can be a Bluetooth™ antenna, an IR antenna or any other antenna capable of sending and receiving electromagnetic signals over short distances for wireless communication.

Figure 8A:
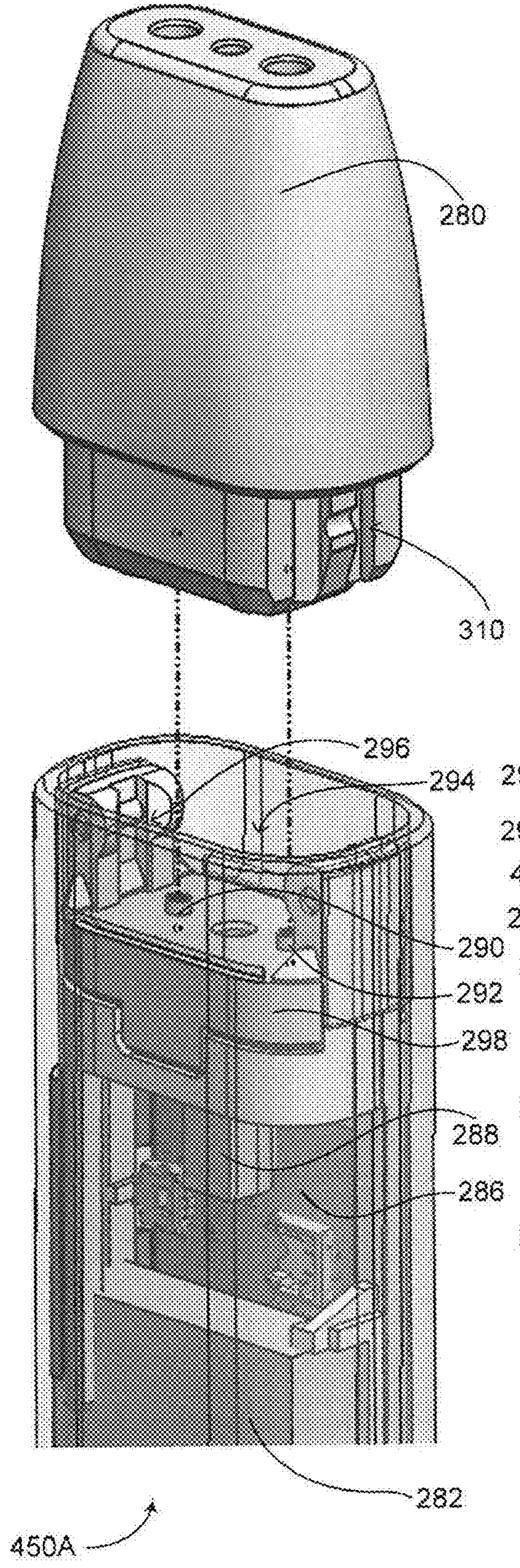
FIGS. 8A-8D are further perspective illustrations of the first example inhalation system of FIGS. 3A-3B, constructed and operative in accordance with an embodiment of the disclosed technique.
Figure 8B:
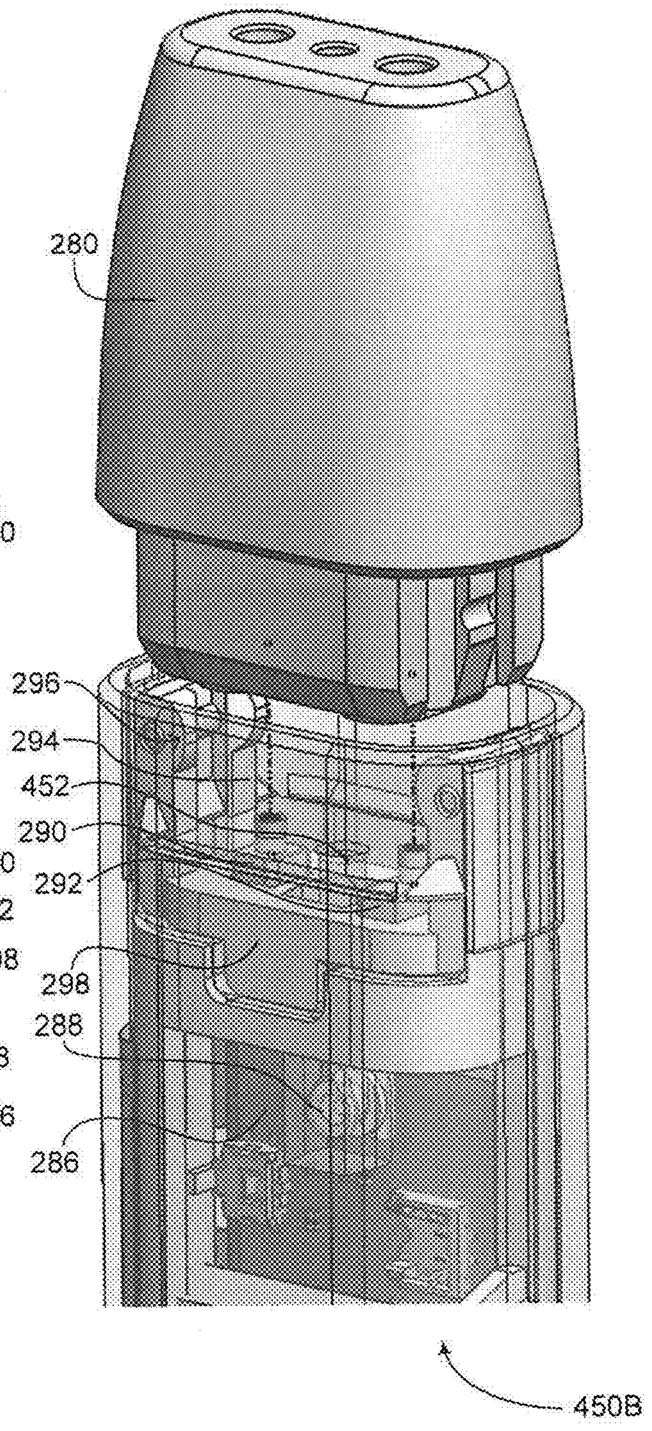
Figure 8C:
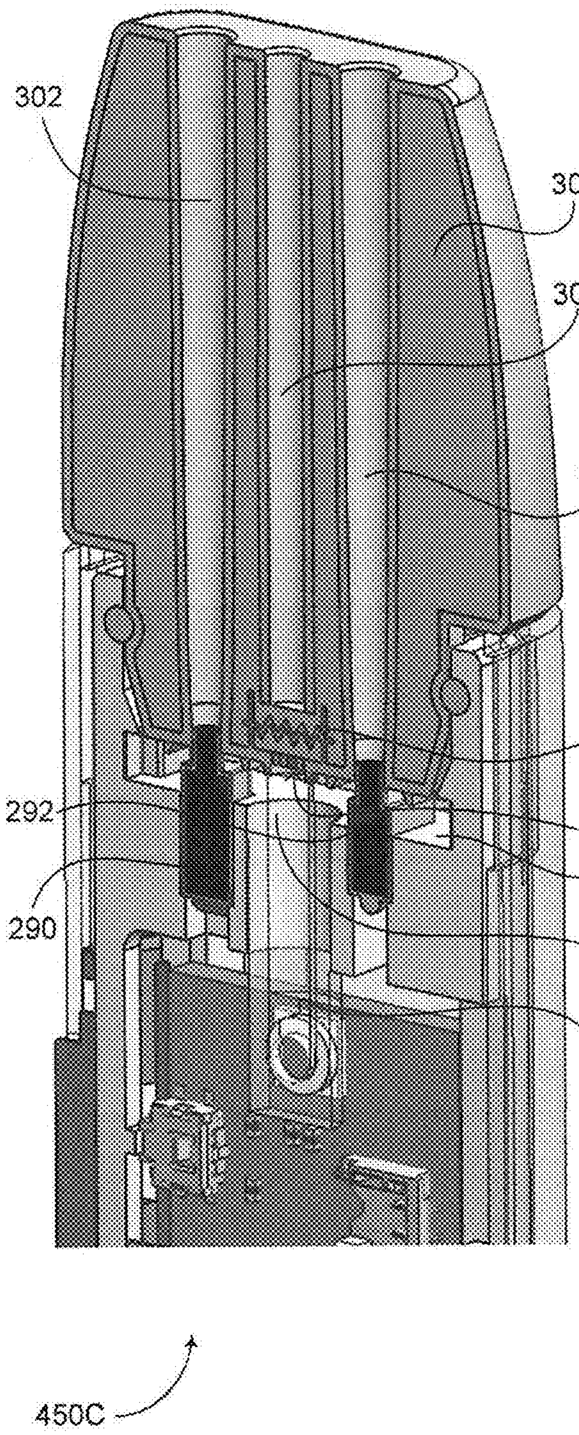
Figure 8D:
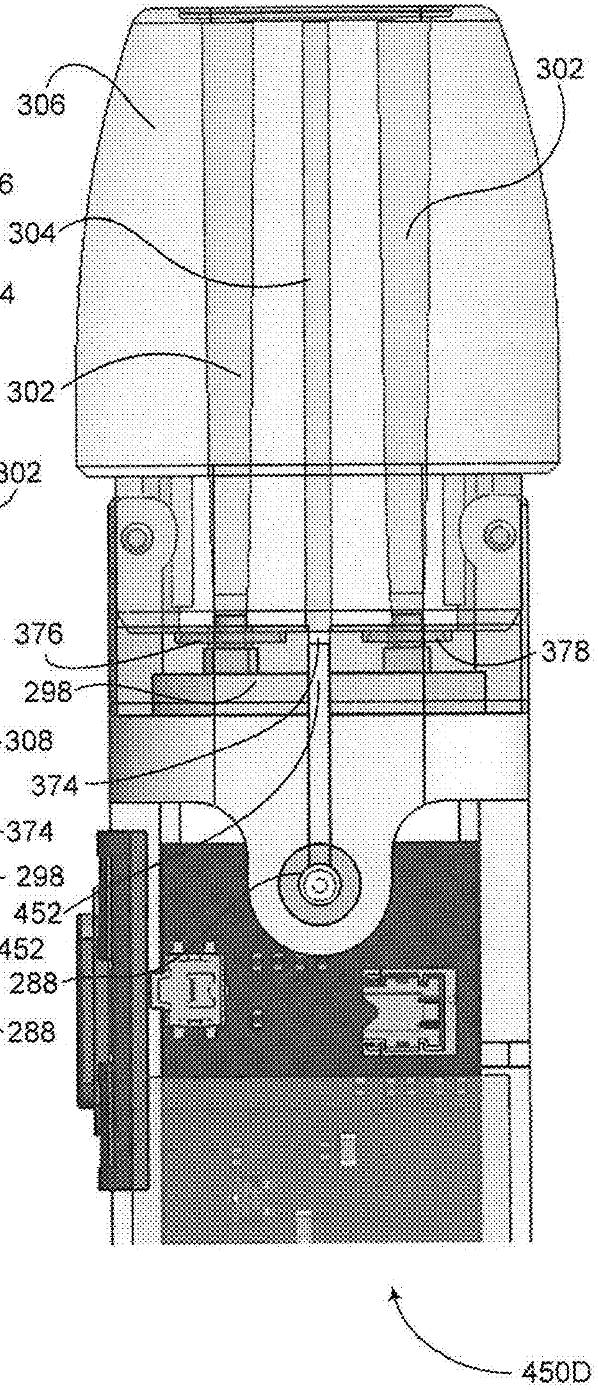

Reference is now made to FIGS. 8A-8D, which are further perspective illustrations of the first example inhalation system of FIGS. 3A-3B, generally referenced 450A-450D, constructed and operative in accordance with an embodiment of the disclosed technique. With reference to FIG. 8A, first example inhalation system 450A is shown in a see-through perspective view, showing the coupling of pod 280 with the device body and in particular its insertion into hollow 294. As can be seen AWG 290 and AWS 292 fit into and couple with acoustic seal 298 and that acoustic seal 298 has an opening into which pressure sensor 288 can be inserted. The complementary shape of both at least one indentation 310 and at least one protrusion 296 are also clearly shown in the figure. With reference to FIG. 8B, first example inhalation system 450B is shown in a see-through perspective view, showing the further coupling of pod 280 with the device body as it is inserted into hollow 294. The distal end 452 of pressure sensor 288 is shown extending through and beyond acoustic seal 298. With reference to FIG. 8C, first example inhalation system 450C is shown in a see-through cross-section perspective view, showing the pod inserted into the device body. As can be seen, the distal ends of waveguides 302 respectively couple with AWG 290 and AWS 292. Shown as well is heating element 308 located just above inlet 374. Distal end 452 of pressure sensor 288 is clearly shown extending through acoustic seal 298 and positioned adjacent to inlet 374. With reference to FIG. 8D, first example inhalation system 450D is shown in a see-through frontal orthogonal view, showing the pod inserted into the device body. Acoustic sealant surfaces 376 and 378 are clearly shown coupling between waveguides 302 and the AWG and AWS. Also shown is the alignment between pressure sensor 288 and airway 304.

Figure 9:
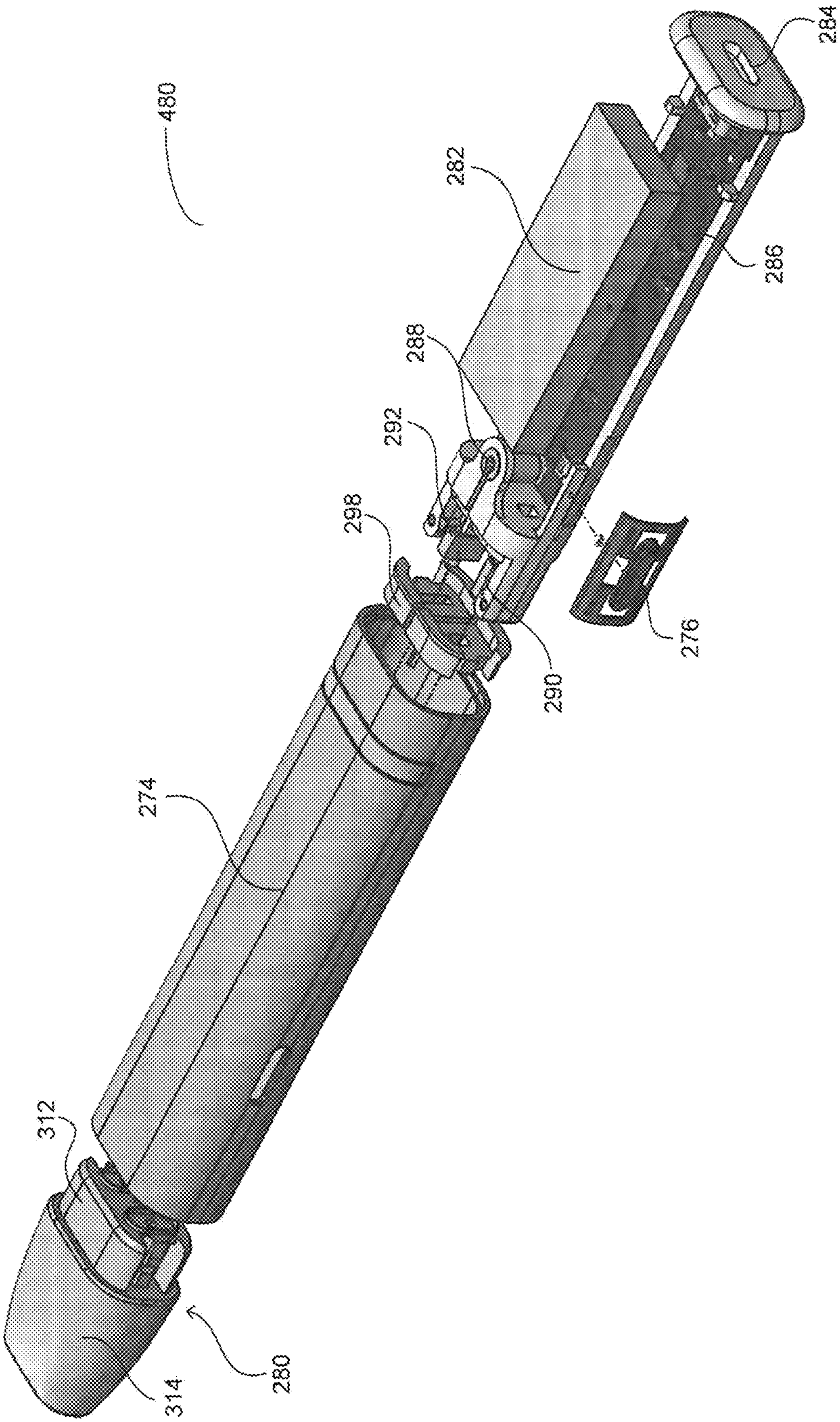
FIG. 9 is an exploded view illustration of the first example inhalation system of FIGS. 3A-3B, constructed and operative in accordance with an embodiment of the disclosed technique.

Reference is now made to FIG. 9, which is an exploded view illustration of the first example inhalation system of FIGS. 3A-3B, generally referenced 480, constructed and operative in accordance with an embodiment of the disclosed technique. FIG. 9 shows how AWG 290, AWS 292 and pressure sensor 288 fit into acoustic seal 298 as well as PCB 286 extending the length of device body 274 and the positioning of battery 282.

Figure 10:
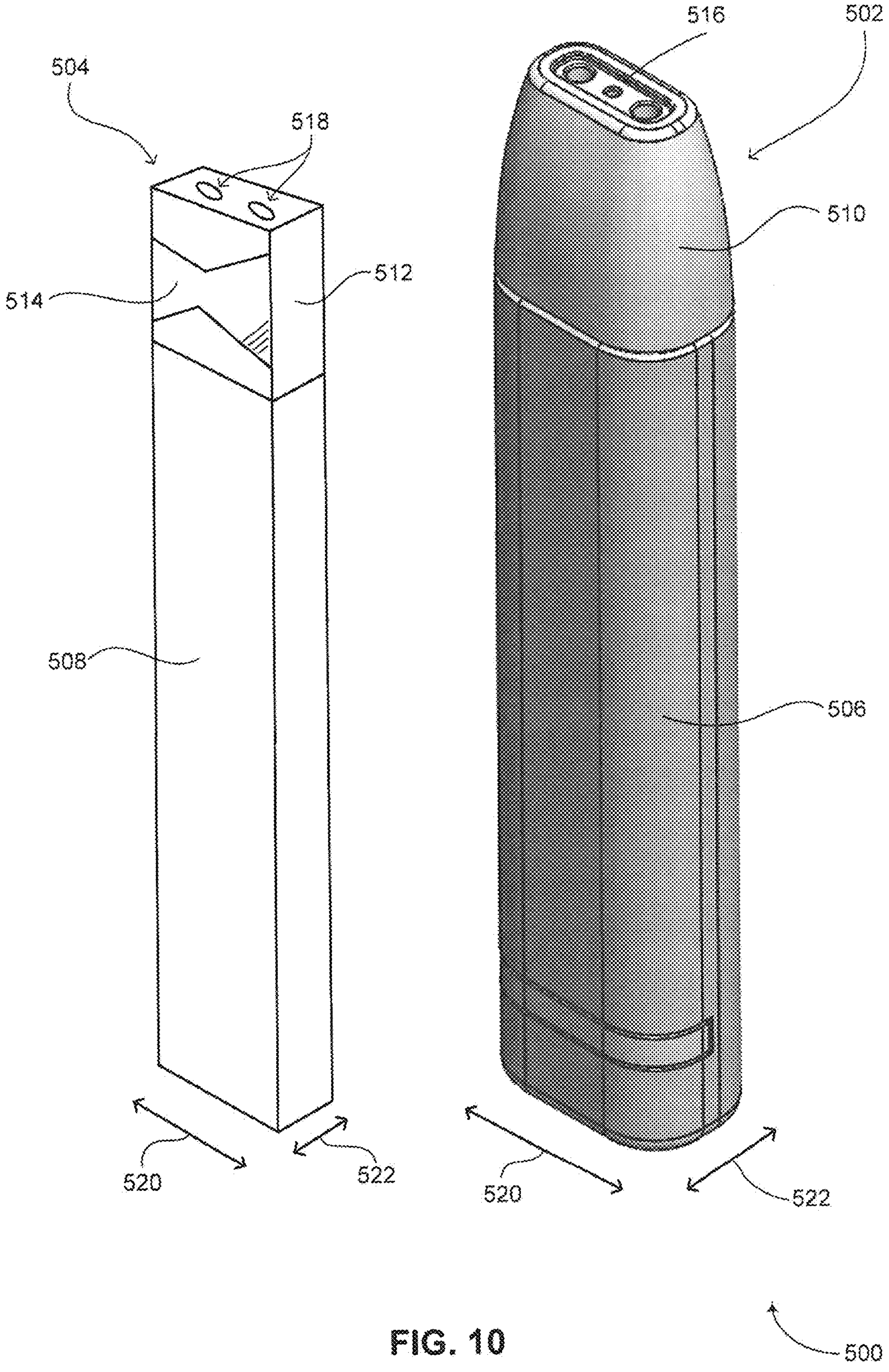
FIG. 10 is a perspective illustration of a first example and second example inhalation system, constructed and operative in accordance with an embodiment of the disclosed technique.

Reference is now made to FIG. 10, which is a perspective illustration of a first example and second example inhalation system, generally referenced 500, constructed and operative in accordance with an embodiment of the disclosed technique. FIG. 10 shows two example design versions of the disclosed technique, a first example inhalation system 502, substantially similar to first example inhalation system 420C (FIG. 7C) and a second example inhalation system 504. As shown, first example inhalation system 502 includes a device body 506 and a mouthpiece 510 which includes a plurality of openings 516 for transmitting and receiving acoustic signals as well as enabling a user to inhale a substance contained within mouthpiece 510. Second example inhalation system 504 likewise includes a device body 508 and a mouthpiece 512 which includes a plurality of openings 518 for transmitting and receiving acoustic signals as well as enabling a user to inhale a substance contained within mouthpiece 512. As shown, mouthpiece 512 is designed to have a transparent window 514 in which the substance can be seen. In case the substance is a liquid, transparent window 514 enables the level of the liquid to be seen by the user. As mentioned above, the disclosed technique may be designed to be handheld and thus should have dimensions which are amenable to being handheld. For example, first and second example inhalation systems may have a base width, as shown by arrow 520, ranging from 10 mm to 30 mm as well as a thickness, as shown by an arrow 522, ranging from 5 mm to 20 mm. The height of first and second example inhalation systems may be between 7 cm to 14 cm. The dimensions provided are merely examples and other dimensions and sizes are possible.

Figure 11:
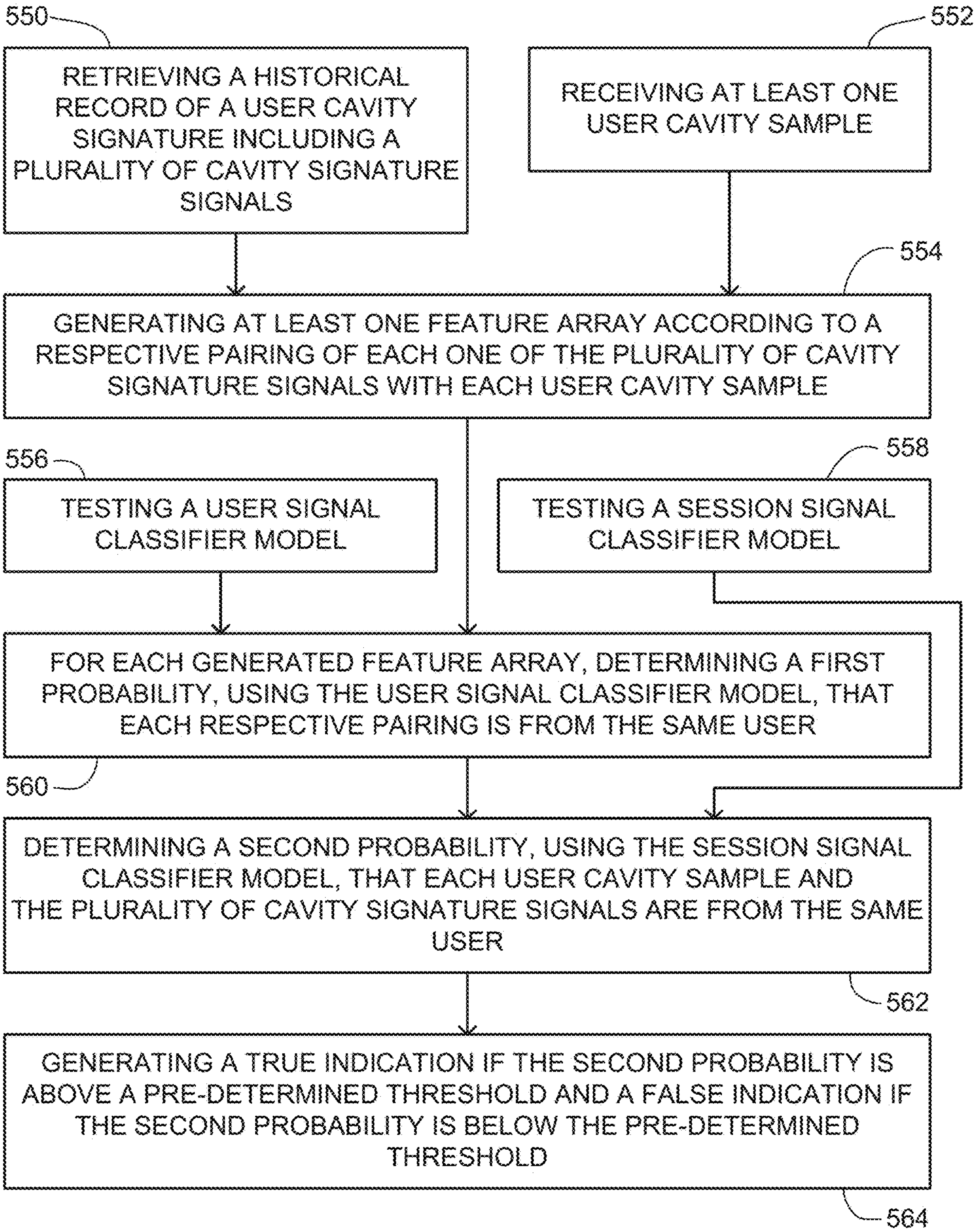
FIG. 11 is a schematic illustration of a method for identify verification, operative in accordance with an embodiment of the disclosed technique.

Reference is now made to FIG. 11, which is a schematic illustration of a method for identify verification, operative in accordance with an embodiment of the disclosed technique. As explained above in FIG. 1, the disclosed technique authenticates a user's cavity signature by transmitting an acoustic signal (a cavity sample) to the user's cavity (e.g., oral, nasal or tympanic) and receiving reflections of the acoustic signal. The frequency response and other parameters and features of the received reflected acoustic signal can be used to test a classifier, such as a machine learning algorithm, classifier model and/or analytical model, to analyze and compare cavity samples to cavity signatures for similarity. In the case of identity verification (ID) of the disclosed technique, a user's cavity signature is first registered and once registered, can then be authenticated when the user uses the system and device of the disclosed technique at a later time. Registration may be performed at a point of sale and may include a procedure of receiving a plurality of cavity samples which are processed to form a cavity signature. The procedures of registration (not shown) may be performed at a point of sale when the buyer registers herself on the device (for example after a seller confirms her age or other use authorization) and optionally with a database of registered users. In FIG. 11, it is assumed that registration and generation of a cavity signature of a user has already been executed. The method of FIG. 11 describes the procedures of performing ID once registration has already been complete. In a procedure 550, a historical record of a user's cavity signature is retrieved. The historical record retrieved can include a plurality of stored cavity samples of transmitted cavity signals as well as the reflections of the cavity signals. These retrieved cavity samples from the registration process can be referred to as cavity signature signals. As an example, 48 cavity signature signals of the user's cavity from the process of registration may be retrieved. This does not necessarily mean that 48 cavity signature signals were used to register the user with the device as more cavity signature signals might have been used in the procedures of registration. Thus, in procedure 550, either all the cavity signature signals, or a subset of the cavity signature signals which were used to register the device are retrieved from the historical record of the user's cavity signature. Procedure 550 can be performed once and the retrieved cavity samples from the cavity signature are then used for one or more sequences of authentication, possibly separate in time and/or location from procedure 550. For example, procedure 550 may even be performed at a point of sale when the buyer registers herself on the device and possibly is required to use it once or more (for example in a demo mode) to ensure successful registration.

In a procedure 552, at least one cavity sample from a user is received. The cavity sample represents an acoustic wave transmitted to and reflected from the user's cavity. The cavity sample may be a plurality of acoustic signals substantially sampling the user's cavity. The cavity sample may include, for example, 3 separate transmitted and received acoustic signals.

According to the method of FIG. 11, the user's cavity sample is to be authenticated based on the historical record of the user's cavity signature. In a procedure 554, at least one feature array is generated according to a respective pairing between each one of the plurality of cavity signature signals retrieved in procedure 550 with each cavity sample taken from the user in procedure 552. Thus if the historical record retrieved of the user's cavity signature included 48 cavity signature signals and 3 cavity samples were taken during the sampling of the user's cavity to authenticate their cavity signature, 144 (3×48) feature arrays are generated in procedure 554 based on a pairing between each cavity signature signal from procedure 550 with each cavity sample of the user from procedure 552. In a procedure 556, a user signal classifier model is tested. The classifier model may be based on a gradient boosting algorithm such as Light Gradient Boosted Machine (LightGBM), XGBoost or Neutral Network package in R or any other specifically designed Neural Network in any known implementation language. Other classifier models as well as analytical models can be used as well. The user signal classifier model is tested to recognize features of a cavity signature based on reflections of acoustic signals from the user's cavity (i.e., the cavity samples) and is used in procedure 560 to verify the user's cavity signature with the cavity samples. As acoustic signals may reflect differently in the same user, due to the particular positioning of the acoustic signal opening from where acoustic signals are transmitted to the user's cavity as well as any voluntary or involuntary movements that may have occurred in the user's cavity when acoustic signals were transmitted to the user's cavity, a signal classifier model is tested to determine identical features in a user's cavity signature based on slight possible variations of the features of the reflected acoustic signals. In a procedure 558, a session signal classifier model is tested. Similar to procedure 556, the classifier model may be based on a gradient boosting algorithm such as LightGBM, XGBoost, Neutral Network package in R, any specifically designed Neural Network in any known implementation language and other classifier models as well as analytical models. The session signal classifier model is different than the user signal classifier model in that it is tested to determine features of a user cavity signature, meaning to extract features from a cavity sample and thus is used in procedure 562 to authenticate the user's cavity sample.

In a procedure 560, for each generated feature array in procedure 554, a first probability is determined, using the user signal classifier model from procedure 556, that each respective pairing between a cavity signature signal and a user cavity sample are from the same user. The better user signal classifier model is tested in procedure 556 (for example, by increasing the number of cavity signature signals and user cavity samples), the higher determined first probability will be. In procedure 560 the user's cavity signature is verified based on the historical record of the user's cavity signature along with the cavity samples transmitted to and reflected from the user's cavity. In a procedure 562, a second probability is determined using the session signal classifier model from procedure 558. The second probability is the determined probability that each user cavity sample from procedure 552 and each cavity signature signal from procedure 550 in the historical record are indeed from the same person. Procedure 562 is thus used to authentic the user cavity sample from procedure 552.

In a procedure 564, the determined second probability is compared to a pre-determined threshold. If the second probability is above the pre-determined threshold then the user cavity sample is authenticated, and a true indication may be generated. If the second probability is below the pre-determined threshold then the user cavity signal is not authenticated, and a false indication may be generated. In an alternative to procedure 564, only a single indication may be provided once the second probability is determined. For example, an indication may be provided only if the second probability is over the pre-determined threshold or only if the second probability is under the pre-determined threshold. The pre-determined threshold may be, for example, 90% for a single user cavity sample and 95% for three user cavity samples. Other pre-determined thresholds are possible and are a matter of design choice. Optionally, in the same device different thresholds may be used to control different functions of the same device. For example, a first pre-determined threshold for use of a recreational substance and a second pre-determined threshold for use of a controlled substance (in an embodiment of the disclosed technique as a device for the delivery of a substance by inhalation).

As shown in the method of FIG. 11, procedures 556 and 558 may occur in a factory setting before any other procedures in the method are executed. The testing of the classifier models, including any determined parameters and/or features, can be stored in the system and device of the disclosed technique, either locally in a memory of the system or device, or remotely in a cloud storage that the system or device can access and retrieve. As mentioned above, the determined parameters and/or features are retrievable by the system and device of the disclosed technique, whether locally on the device or remotely from another location. It is noted that the method of FIG. 11 can be used to authenticate a system or device embodiment of the disclosed technique with a particular user.

The method of FIG. 11 enables a user to verify their cavity signature with a device or system of the disclosed technique. As mentioned above, machine learning algorithms embedded within (or at least retrievable from) the device or system of the disclosed technique can then be used to authenticate a user based on their registered cavity signature for repeat use of the system or device. As described in procedure 550, for first use, the method requires that a historical record of their cavity signature be retrieved, which might include 48 samples of their cavity signature or fewer cavity signature samples (such as 10) or more cavity signature samples.

Figure 12:
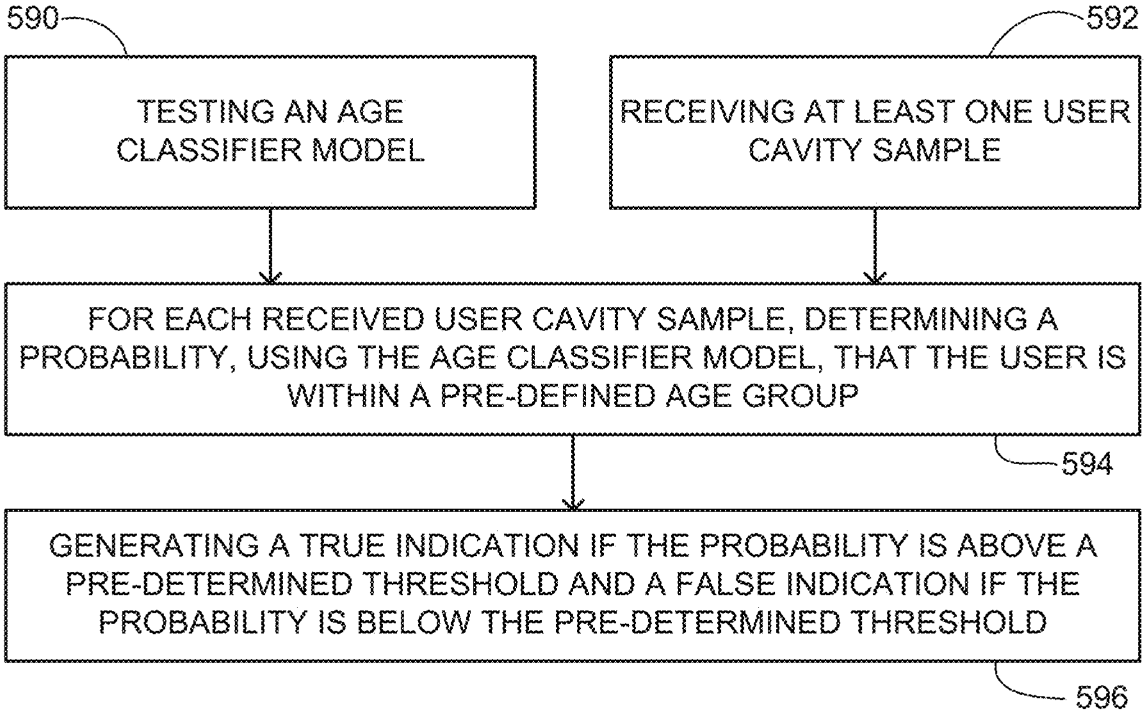
FIG. 12 is a schematic illustration of a method for age verification, operative in accordance with an embodiment of the disclosed technique.

Reference is now made to FIG. 12, which is a schematic illustration of a method for age verification, operative in accordance with an embodiment of the disclosed technique. In a procedure 590, an age classifier model is tested. As mentioned above, the classifier may be a boosting gradient algorithm, a classifier model or an analytical model. The age classifier model is tested to identify features in reflected acoustic signals of different aged users. Testing can be done a priori in a laboratory setting where different aged users, such as children, adolescents and/or adults use the system and device of the disclosed technique to provide reflections of acoustic signals from their oral, nasal and/or tympanic cavities. As the number of samples inputted into the age classifier model increases, the accuracy of determining features of a cavity signature which is age (or age group) specific increases. In an embodiment of the disclosed technique, procedure 590 can be ongoing with ever increasing numbers of users of the disclosed technique registering their cavity signatures, as per the method of FIG. 11, with a central database. Given additional information about each registered user, such as their age, the features of the cavity signature of users of a particular age, or age group, can be discerned and determined and the age classifier model can be constantly improved in terms of accuracy. In a procedure 592, at least one user cavity sample is received, similar to procedure 552 (FIG. 11).

In a procedure 594, for each received user cavity sample, a probability is determined, using the age classifier model of procedure 590, if the user is in a pre-defined age group. The probability is determined by a comparison and analysis of the features of the received user cavity sample to the features in the age classifier model. As mentioned above, the age classifier model may include features defining different age groups, such as non-permitted users under age 14 (children), permitted adolescent users aged 14-16 and/or 16-18 (adolescents) as well as permitted adult users 18+ years and/or 21+ years (adults). In an alternative to procedure 594, the age classifier model of procedure 590 can be used to determine the probability that a received user cavity sample indicates a particular age (or age group) of the user, or indicates a pre-defined minimal and/or maximal age of the user. In general, the probability determined is the probability of a cavity sample being a true member of a class. The probability of the cavity sample not being a true member of the class can thus be determined by subtracting from 100%. The age classifier model of procedure 590 generally returns a binary result as to what percent probability a cavity sample is in a given age group and thus what percent probability a cavity sample is not in the given age group. It is noted as well that different pre-trained classifiers on the same cavity sample might yield different results. Thus an age classifier model determining a probability X that a cavity sample is in a child age group, thereby yielding a probability Y that the cavity sample is not in a child age group (where X+Y=100%), might yield different results for an age classifier model determining a probability Z that a cavity sample is in an adult age group, thereby yielding a probability A that the cavity sample is not in an adult age group (where Z+A=100% and Z does not necessarily equal Y and Z does not necessarily equal X).

In a procedure 596, a true indication may be generated if the determined probability in procedure 594 is above a pre-determined threshold and thus the user is authenticated as a permitted user. However, if the determined probability is below the pre-determined threshold then a false indication may be generated and the user is not authenticated as a permitted user and the system or device of the disclosed technique may not operate, may shut down or may have limited functionality. In an alternative to procedure 596, only a single indication may be provided once the probability is determined. For example, an indication may be provided only if the probability is over the pre-determined threshold or only if the probability is under the pre-determined threshold. The pre-determined threshold may be, for example, 90% for a single user cavity sample and 95% for three user cavity samples. Other pre-determined thresholds are possible and are a matter of design choice.

As mentioned in FIG. 11, the features of the age classifier model may be stored locally in a memory on the system or device or may be stored remotely on a cloud storage, in which case, the system or device of the disclosed technique would require wireless connectivity to the cloud storage to function properly. As mentioned above, according to the disclosed technique, the features of the age classifier model are retrievable, whether locally or remotely.

As mentioned above, in either the case of ID or AV, the registered cavity signature of a user or the features of the cavity signature of a permitted user and/or a non-permitted user, may be stored locally on the device or system of the disclosed technique and/or remotely. In the case of AV, intrinsic features of the cavity signature of a permitted user do not need to be used. The age classifier model is tested to determined features of the cavity signature of permitted users which are unique compared to the features of the cavity signature of non-permitted users. Thus, in the case of AV, features of non-permitted users can be used to authenticate a user. Also as mentioned above, the determined features of the age classifier model of procedure 590 can be updated as a database of users of the system and device of the disclosed technique and their cavity signatures grows. Updated features for the age classifier model may be provided to a system or device of the disclosed technique wirelessly.

It will be appreciated that in an embodiment both ID and AV are enabled. For example, a person who is within a permitted age group may use the device even if not registered to it in addition to a registered user. In an embodiment, any person of the permitted age group is authorized unless registered as a restricted user. In an embodiment, AV authorization may be used as a first step to ID registration. One benefit of such an embodiment may be that after a device is allocated to a user, the ID testing may take place on the device or system while AV testing requires obtaining data from a plurality of users.

It will be appreciated by persons skilled in the art that the disclosed technique is not limited to what has been particularly shown and described hereinabove. Rather the scope of the disclosed technique is defined only by the claims, which follow.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A breathalyzer which verifies identity of a user, comprising:
- a mouthpiece;
- a sample collector for collecting a sample of exhaled air of the user;
- an acoustic subsystem, for producing at least one acoustic signal and receiving at least one reflection of said at least one acoustic signal;
- an analyzer of said exhaled air to estimate a content of a substance in the user's blood;
- a processor, coupled with said acoustic subsystem, for authenticating the user based on the reflection of said at least one acoustic signal, and
- a communication module, for communicating with a key fob of a vehicle and permitting use of the vehicle device based on the authentication of the user and the estimated the content of the substance in the user's blood.

2. The breathalyzer of claim 1, further comprising a communication module, for communicating with an associated device and permitting access to said associated device based on the authentication of the user and the estimated content of the substance in the user's blood.

3. The breathalyzer of claim 1, wherein said acoustic subsystem comprises:
- an acoustic wave generator, for generating at least one acoustic signal; and an acoustic wave sensor, for receiving at least one reflection of said at least one acoustic signal.

4. The breathalyzer of claim 1, wherein said substance is alcohol.

5. The breathalyzer of claim 1, wherein said mouthpiece comprises an acoustic signal opening and a reflection signal opening.

6. The breathalyzer of claim 3, further comprising:
- an output acoustic waveguide, coupled between said acoustic wave generator and said acoustic signal opening, for transmitting said at least one acoustic signal to said user; and
- an input acoustic waveguide, coupled between said acoustic wave sensor and said reflection signal opening, for receiving said at least one reflection of said at least one acoustic signal.

7. The breathalyzer of claim 1, further comprising a memory, configured to store oral cavity authentication data representative of at least one feature of the user, retrievable by said processor, wherein said processor is configured to compare said reflection with said retrievable cavity authentication data stored in said memory and to generate an indication whether said analyzed at least one reflection matches said retrievable cavity authentication data above a pre-determined threshold.

8. The breathalyzer according to claim 7, wherein said oral cavity authentication data comprises an oral signature of at least one specific user.

9. The breathalyzer according to claim 7, wherein said oral cavity authentication data includes an oral signature comprising at least feature selected from
- a group consisting of:
- a permitted user;
- a restricted user; and
- an underage user.

10. A method of controlling operation of a device by a user comprising:

estimating a blood level of a substance in the user using a breathalyzer;

authenticating the user using an acoustic element in the breathalyzer which receives an acoustic signal emitted from the oral cavity of the user; and controlling operation of the device based on authentication of the user and an estimated blood level of the substance, wherein said controlling operation comprises enabling a key fob upon authentication of the user and confirmation of sobriety.

11. The method of claim 10, wherein said authenticating comprises analyzing said received acoustic signal to determine if the received acoustic signal matches an oral signature of the user above a pre-determined threshold.

12. The method of claim 10, wherein said controlling operation comprises enabling or disabling activation of the device.

13. The method of claim 10, further comprising registering the user prior to the authenticating, said registering comprises:

receiving an acoustic signal emitted from the oral cavity of the user, using said acoustic element; and storing the received acoustic signal data in association with data of a feature of the user as the oral signature of the user.

14. The method of claim 10, further comprising accessing a memory for storing oral signatures.

15. The method of claim 14, wherein the analyzing comprises comparing the received acoustic signal to an oral signature retrieved from the memory.

16. The method of claim 10, wherein the authenticating further includes transmitting an acoustic signal to the oral cavity of the user prior to the receiving.

17. The method of claim 10, wherein the substance is alcohol.

* * * * *